(12) United States Patent
Raymond et al.

(10) Patent No.: US 8,409,145 B2
(45) Date of Patent: Apr. 2, 2013

(54) INSERTION DEVICES FOR INFUSION DEVICES

(75) Inventors: Randy Stephen Raymond, Eagle Mountain, UT (US); Joseph K. Walker, Pleasant Grove, UT (US); Dan Lopez, Vernal, UT (US); Dee E. Warren, Draper, UT (US)

(73) Assignee: Tecpharma Licensing AG (CH)

( * ) Notice: Subject to any disclaimer, the term of this patent is extended or adjusted under 35 U.S.C. 154(b) by 494 days.

(21) Appl. No.: 12/208,313

(22) Filed: Sep. 10, 2008

(65) Prior Publication Data

US 2009/0124979 A1    May 14, 2009

Related U.S. Application Data

(60) Provisional application No. 60/973,134, filed on Sep. 17, 2007, provisional application No. 61/042,232, filed on Apr. 3, 2008.

(51) Int. Cl.
*A61M 5/178* (2006.01)

(52) U.S. Cl. .............. 604/164.12; 604/157; 604/164.01; 604/164.04; 604/164.07; 604/288.01; 604/288.02; 604/288.03; 604/288.04

(58) Field of Classification Search ............ 604/164.01, 604/164.04, 164.12, 174, 175, 180, 288.01–288.01, 604/156, 157
See application file for complete search history.

(56) References Cited

U.S. PATENT DOCUMENTS

| | | |
|---|---|---|
| 3,094,989 A | 6/1963 | Stauffer |
| D208,611 S | 9/1967 | Smith, Jr. |
| 3,467,088 A | 9/1969 | Robinson |
| 3,757,771 A | 9/1973 | Ruegg et al. |
| 3,820,542 A | 6/1974 | Hurschman |
| 4,068,659 A | 1/1978 | Moorehead |
| 4,068,660 A | 1/1978 | Beck |
| 4,111,190 A | 9/1978 | Plumridge |
| 4,164,224 A | 8/1979 | Hastings |
| 4,205,565 A | 6/1980 | Smith |
| 4,227,528 A | 10/1980 | Wardlaw |
| 4,326,519 A | 4/1982 | D'Alo et al. |
| 4,517,978 A | 5/1985 | Levin et al. |
| 4,553,962 A | 11/1985 | Brunet |
| 4,753,636 A | 6/1988 | Free |
| RE32,922 E | 5/1989 | Levin et al. |
| 4,850,973 A | 7/1989 | Jordan et al. |

(Continued)

FOREIGN PATENT DOCUMENTS

| | | |
|---|---|---|
| WO | WO 97/42882 | 11/1997 |
| WO | WO 99/33504 | 7/1999 |

(Continued)

*Primary Examiner* — Bhisma Mehta
*Assistant Examiner* — Larry R Wilson
(74) *Attorney, Agent, or Firm* — Knobbe Martens Olson & Bear LLP

(57) ABSTRACT

An insertion device for inserting an infusion device at least partially into skin for subcutaneous infusion can comprise a sleeve having a lower surface that is configured to engage the skin, a shuttle or carriage to carry the infusion device between a retracted position and an advanced position; at least a first biasing member to urge the shuttle or carriage toward the advanced position, and an actuator to cause the first biasing member to urge the carriage from the retracted position to the advanced position. In some embodiments, the insertion device can further comprise a hub and at least a second biasing member to urge the hub away from the shuttle or carriage. In some embodiments, the insertion device can further comprise a needle attached to the hub. Methods for inserting an infusion device and various other features that can be comprised by an insertion device are also disclosed.

22 Claims, 30 Drawing Sheets

U.S. PATENT DOCUMENTS

| | | | |
|---|---|---|---|
| 4,858,607 A | 8/1989 | Jordan et al. | |
| 4,862,885 A | 9/1989 | Cumming | |
| 4,886,499 A | 12/1989 | Cirelli et al. | |
| 4,913,704 A | 4/1990 | Kurimoto | |
| 4,917,669 A | 4/1990 | Bonaldo | |
| 4,994,042 A | 2/1991 | Vadher | |
| 5,065,754 A | 11/1991 | Jensen | |
| 5,112,317 A | 5/1992 | Michel | |
| 5,141,496 A | 8/1992 | Dalto et al. | |
| 5,147,375 A | 9/1992 | Sullivan et al. | |
| 5,167,632 A | 12/1992 | Eid et al. | |
| 5,167,645 A | 12/1992 | Castillo | |
| RE34,223 E | 4/1993 | Bonaldo | |
| 5,222,947 A | 6/1993 | D'Amico | |
| 5,246,426 A | 9/1993 | Lewis et al. | |
| 5,269,799 A | 12/1993 | Daniel | |
| 5,279,579 A | 1/1994 | D'Amico | |
| 5,279,586 A | 1/1994 | Balkwill | |
| 5,284,474 A | 2/1994 | Adair | |
| 5,299,347 A | 4/1994 | Decker | |
| 5,300,030 A | 4/1994 | Crossman et al. | |
| 5,350,392 A | 9/1994 | Purcell et al. | |
| 5,368,045 A | 11/1994 | Clement et al. | |
| 5,368,047 A | 11/1994 | Suzuki et al. | |
| 5,376,082 A | 12/1994 | Phelps | |
| 5,391,151 A | 2/1995 | Wilmot | |
| 5,423,760 A | 6/1995 | Yoon | |
| 5,429,613 A | 7/1995 | D'Amico | |
| 5,507,757 A | 4/1996 | Sauer et al. | |
| 5,540,709 A | 7/1996 | Ramel | |
| 5,545,143 A | 8/1996 | Fischell et al. | |
| 5,563,363 A | 10/1996 | Soulaigre et al. | |
| 5,584,847 A | 12/1996 | Duluco et al. | |
| 5,591,188 A | 1/1997 | Waisman | |
| 5,651,791 A | 7/1997 | Zavlodaver et al. | |
| 5,665,071 A | 9/1997 | Wyrick | |
| 5,713,876 A | 2/1998 | Bogert et al. | |
| 5,741,234 A | 4/1998 | Aboul-Hosn | |
| 5,741,288 A | 4/1998 | Rife | |
| 5,741,292 A | 4/1998 | Mendius | |
| 5,851,197 A | 12/1998 | Marano et al. | |
| 5,865,806 A | 2/1999 | Howell | |
| 5,913,869 A | 6/1999 | Reil | |
| 5,925,057 A | 7/1999 | Blomdahl | |
| 5,957,895 A | 9/1999 | Sage et al. | |
| 5,957,896 A | 9/1999 | Bendek et al. | |
| 6,017,328 A | 1/2000 | Fischell et al. | |
| D422,356 S | 4/2000 | Marano et al. | |
| 6,074,369 A | 6/2000 | Sage et al. | |
| 6,090,068 A | 7/2000 | Chanut | |
| 6,093,172 A | 7/2000 | Funderburk et al. | |
| 6,099,503 A | 8/2000 | Stradella | |
| 6,293,925 B1 | 9/2001 | Safabash et al. | |
| 6,517,517 B1 | 2/2003 | Farrugia et al. | |
| 6,607,509 B2 | 8/2003 | Bobroff et al. | |
| 6,699,218 B2 | 3/2004 | Flaherty et al. | |
| 6,702,779 B2 | 3/2004 | Connelly et al. | |
| 6,830,562 B2 | 12/2004 | Mogensen et al. | |
| 6,926,694 B2 | 8/2005 | Marano-Ford et al. | |
| 6,939,330 B1 | 9/2005 | McConnell-Montalvo et al. | |
| 6,991,619 B2 | 1/2006 | Marano-Ford et al. | |
| 6,991,620 B2 | 1/2006 | Marano-Ford et al. | |
| 6,997,907 B2 | 2/2006 | Safabash et al. | |
| 7,022,108 B2 | 4/2006 | Marano-Ford et al. | |
| 7,052,483 B2 | 5/2006 | Wojcik | |
| 7,056,302 B2 | 6/2006 | Douglas | |
| 7,097,631 B2 | 8/2006 | Trautman et al. | |
| 7,128,730 B2 | 10/2006 | Marano-Ford et al. | |
| 7,153,275 B2 | 12/2006 | Blondeau | |
| 7,207,974 B2 | 4/2007 | Safabash et al. | |
| 7,258,678 B2 | 8/2007 | Wilkinson | |
| 7,318,816 B2 | 1/2008 | Bobroff et al. | |
| 7,329,239 B2 | 2/2008 | Safabash et al. | |
| 7,381,184 B2 | 6/2008 | Funderburk et al. | |
| 7,407,493 B2 | 8/2008 | Cane' | |
| 7,455,663 B2 | 11/2008 | Bikovsky | |
| 7,569,050 B2 | 8/2009 | Moberg et al. | |
| 7,582,059 B2 | 9/2009 | Funderburk et al. | |
| 7,585,287 B2 | 9/2009 | Bresina et al. | |
| 7,618,396 B2 | 11/2009 | Slate et al. | |
| 7,621,395 B2 | 11/2009 | Mogensen et al. | |
| 7,641,649 B2 | 1/2010 | Moberg et al. | |
| 7,648,494 B2 | 1/2010 | Kornerup et al. | |
| 7,670,314 B2 | 3/2010 | Wall et al. | |
| 7,682,338 B2 | 3/2010 | Griffin | |
| 7,686,787 B2 | 3/2010 | Moberg et al. | |
| 7,699,807 B2 | 4/2010 | Faust et al. | |
| 7,731,691 B2 | 6/2010 | Cote et al. | |
| 7,736,338 B2 | 6/2010 | Kavazov et al. | |
| 7,815,607 B2 | 10/2010 | Rutti et al. | |
| 7,828,771 B2 | 11/2010 | Chiang et al. | |
| 7,879,010 B2 | 2/2011 | Hunn et al. | |
| 7,909,791 B2 | 3/2011 | Liniger et al. | |
| 2003/0109829 A1 | 6/2003 | Mogensen et al. | |
| 2003/0199823 A1 | 10/2003 | Bobroff et al. | |
| 2004/0002682 A1 | 1/2004 | Kovelman et al. | |
| 2004/0158207 A1* | 8/2004 | Hunn et al. | 604/164.01 |
| 2004/0204687 A1 | 10/2004 | Mogensen et al. | |
| 2005/0043687 A1 | 2/2005 | Mogensen et al. | |
| 2005/0065466 A1 | 3/2005 | Vedrine | |
| 2005/0101932 A1* | 5/2005 | Cote et al. | 604/506 |
| 2005/0124936 A1 | 6/2005 | Mogensen et al. | |
| 2006/0129123 A1 | 6/2006 | Wojcik | |
| 2006/0161108 A1 | 7/2006 | Mogensen et al. | |
| 2006/0229559 A1 | 10/2006 | Marano-Ford et al. | |
| 2006/0229560 A1 | 10/2006 | Marano-Ford et al. | |
| 2007/0021729 A1 | 1/2007 | Mogensen et al. | |
| 2007/0093754 A1* | 4/2007 | Mogensen et al. | 604/164.01 |
| 2007/0156094 A1* | 7/2007 | Safabash et al. | 604/164.12 |
| 2008/0039794 A1 | 2/2008 | Kornerup et al. | |
| 2008/0051714 A1 | 2/2008 | Moberg et al. | |
| 2008/0215035 A1 | 9/2008 | Yodfat et al. | |
| 2008/0269683 A1 | 10/2008 | Bikovsky | |
| 2008/0269687 A1 | 10/2008 | Chong et al. | |
| 2009/0082728 A1 | 3/2009 | Bikovsky | |
| 2009/0198215 A1 | 8/2009 | Chong et al. | |
| 2009/0218243 A1 | 9/2009 | Gyrn et al. | |
| 2010/0004597 A1 | 1/2010 | Gyrn et al. | |
| 2010/0049014 A1 | 2/2010 | Funderburk et al. | |
| 2010/0130943 A1 | 5/2010 | Moberg et al. | |
| 2010/0152658 A1 | 6/2010 | Hanson et al. | |
| 2010/0152674 A1 | 6/2010 | Kavazov et al. | |
| 2010/0286615 A1 | 11/2010 | Gyrn et al. | |
| 2011/0040254 A1 | 2/2011 | Gyrn et al. | |
| 2011/0040263 A1 | 2/2011 | Hordum et al. | |

FOREIGN PATENT DOCUMENTS

| | | |
|---|---|---|
| WO | WO 02/081012 A2 | 10/2002 |
| WO | WO 02/100457 A2 | 12/2002 |
| WO | WO 03/026728 A1 | 4/2003 |
| WO | WO 2008/078318 A2 | 7/2008 |

\* cited by examiner

INSERTION DEVICES FOR INFUSION DEVICES

RELATED APPLICATIONS

This application claims the benefit under 35 U.S.C. §119(e) of U.S. Provisional Application No. 60/973,134, filed Sep. 17, 2007, titled INSERTION DEVICE FOR AN INFUSION SET, and U.S. Provisional Application No. 61/042,232, filed Apr. 3, 2008, titled INSERTION DEVICE FOR AN INFUSION SET. The entire contents of each of these applications are hereby incorporated by reference herein and made a part of this specification.

BACKGROUND

1. Field

The present disclosure relates to devices that facilitate insertion of infusion devices, such as infusion sets, into a subject, and more particularly devices for inserting infusion devices at least partially into a person's skin.

2. Description of the Related Art

Subcutaneous injection is a standard method for the delivery of medication into a patient's body. To facilitate frequent or continuous subcutaneous injection of medication, subcutaneous injection ports are often used. Such injection ports include a component that extends through the skin and may remain in place for several days. Currently, a major application of such injection ports is to provide continuous delivery of medication, such as insulin, from portable pumps carried with the patient.

Subcutaneous injection ports generally require a sharp, rigid needle to pierce the person's skin when initially attached to the person. In many cases the needle is withdrawn and a soft plastic cannula remains inside the body for an extended period. In other cases, the rigid needle can be hollow and remain in the patient to deliver medication.

Subcutaneous injection ports are sometimes inserted into the skin using an insertion device.

SUMMARY OF THE DISCLOSURE

Prior insertion devices do not adequately address the needs of users. Some users may suffer from conditions, such as diabetic neuropathy. It can be advantageous for an insertion device for an infusion device to be easily grasped and operated by diabetics suffering from diabetic neuropathy. Diabetic neuropathy can cause numbness, loss of feeling and muscle weakness in the hands and fingers making fine motor control difficult. At times, a user may need to insert an infusion device at a location on the user's body which may complicate insertion, e.g., on a user's side or back. In some instances, an adult may need to assist a child in placing an infusion device on the child's body. In these instances and others, it can be beneficial for an insertion device for an infusion device to require a minimum number of operational steps while providing safe operation and disposal. Such an insertion device may advantageously minimize the possibility of accidental needle sticks and/or premature activation of the insertion device. Accordingly, it can be advantageous for an insertion device to insert an infusion device, such as an infusion set, quickly, safely, and conveniently.

Thus, in accordance with at least one of the embodiments disclosed herein, a device for inserting an infusion device through skin for subcutaneous infusion comprises a sleeve, a shuttle, at least a first biasing member, a hub, a needle, at least a second biasing member, and an actuator.

The sleeve can have an upper surface and a lower surface. The lower surface of the sleeve can be configured to engage skin.

The shuttle can comprise a receptacle for accommodating an infusion device, at least a first movement-restraining arm, and a least a first hub-retaining arm. The shuttle can be movable between a retracted position and an advanced position. The first movement-restraining arm can engage the upper surface of the sleeve when the shuttle is in the retracted position to inhibit movement of the shuttle toward the advanced position. The first biasing member can be operatively connected to the shuttle to urge the shuttle toward the advanced position.

The hub can have an upper side and a lower side. The hub can be movable between a first position and a second position with respect to the shuttle. The first hub-retaining arm of the shuttle can inhibit movement of the hub away from the shuttle when the hub is in the first position.

The needle can have an upper end and a lower end. The upper end can be fixedly attached to the lower side of the hub. The lower end can be configured to pierce skin. The lower end of the needle can extend below the lower surface of the sleeve when the shuttle is in the advanced position and the hub is in the first position. The lower end of the needle can be positioned above the lower surface of the sleeve when the hub is in the second position. The second biasing member can be operatively connected to the hub to urge the hub upwardly from the shuttle away from the lower surface of the sleeve.

The actuator can be movably attached to the sleeve such that, when the first movement-restraining arm is engaged with the upper surface, advancement of the actuator toward the sleeve permits disengagement the first movement-restraining arm of the shuttle from the upper surface of the sleeve. Disengagement of the first movement-restraining arm of the shuttle from the upper surface of the sleeve can allow the first biasing member to move the shuttle from the retracted position to the advanced position. Movement of the shuttle from the retracted position to the advanced position can allow the first hub-retaining arm of the shuttle to release the hub such that the second biasing member moves the hub from the first position to the second position.

In accordance with at least one of the embodiments disclosed herein, an inserter for placing an infusion device at least partially into skin can comprise a sleeve, a carriage, at least at first biasing member, a hub, a needle, at least a second biasing member, and an actuator.

The sleeve can have a bottom surface. The bottom surface can be configured to engage skin.

The carriage can carry the infusion device. The carriage can be positioned at least partially within the sleeve. The carriage can be movable between a retracted position and an advanced position. The lowest portion of the infusion device can be spaced upwardly from the bottom surface of the sleeve when the carriage is in the retracted position. The bottom portion of the infusion device can extend below the lower surface of the sleeve when the carriage is in the advanced position. The first biasing member can be operatively connected to the carriage to urge the carriage toward the advanced position The hub can be movable between a first position and a second position with respect to the carriage. The needle can have an upper end and a lower end. The upper end can be fixedly attached to the lower side of the hub. The lower end can be configured to pierce skin. The needle can extend below the carriage when the hub is in the first position. The lower end of the needle can extend no lower than the carriage when the hub is in the second position. The second biasing member can be operatively connected to the hub to urge the hub upwardly from the carriage away from the lower surface of the sleeve.

The actuator can be operatively connected to the sleeve to cause the first biasing member to move the carriage from the retracted position to the advanced position. Movement of the carriage from the retracted position toward the advanced position permits the hub to move from the first position to the second position.

In accordance with at least one of the embodiments disclosed herein, an inserter for placing an infusion device at least partially into skin can comprise a housing, I carriage, at least at first biasing member, and an actuator.

The housing can have a bottom surface. The bottom surface can be configured to engage skin.

The carriage can be configured to carry an infusion device. The carriage can be positioned at least partially within the housing. The carriage can be movable between a retracted position and an advanced position. The lowest portion of the infusion device can be spaced upwardly from the bottom surface of the housing when the carriage is in the retracted position. The bottom portion of the infusion device can extend below the lower surface of the housing when the carriage is in the advanced position. The carriage can comprise at least one movable member for engaging the infusion device to inhibit release of the infusion device from the carriage before the carriage moves from the retracted position toward the advanced position. The first biasing member can be operatively connected to the carriage to urge the carriage toward the advanced position.

The actuator can be operatively connected to the housing to cause the first biasing member to move the carriage from the retracted position to the advanced position. Movement of the carriage from the retracted position toward the advanced position can cause the hub to move from the first position to the second position.

These and other embodiments of the present invention will become readily apparent to those skilled in the art from the following detailed description of the preferred embodiments having reference to the attached figures, the invention not being limited to any particular preferred embodiment(s) disclosed.

Neither this summary nor the following detailed description purports to define the invention. The invention is defined by the claims.

BRIEF DESCRIPTION OF THE DRAWINGS

Specific embodiments will now be described with reference to the drawings, which are intended to illustrate and not limit the various features of the invention.

DETAILED DESCRIPTION OF SPECIFIC EMBODIMENTS

Figure 1:
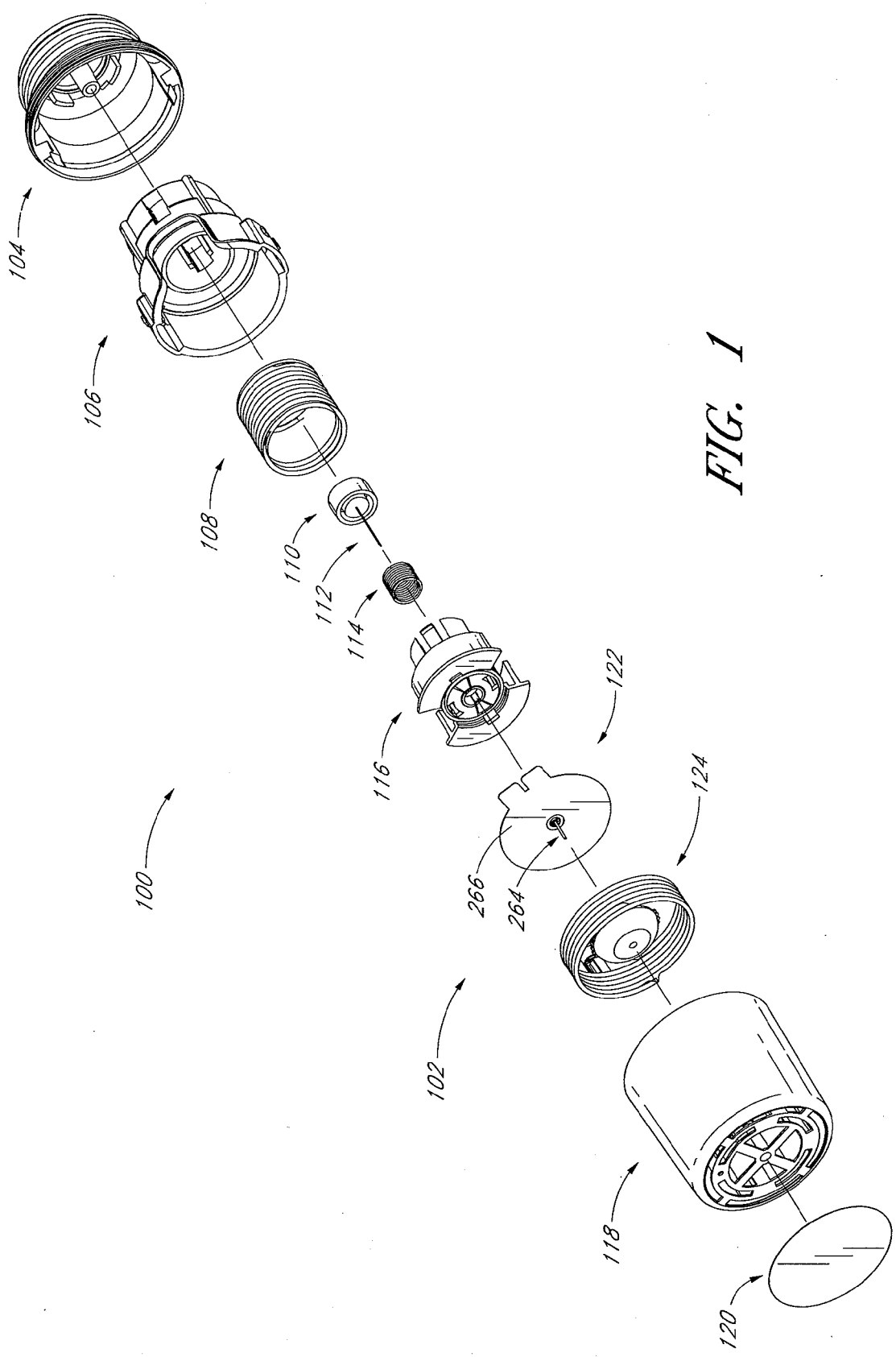
FIG. 1 is an exploded perspective view of an insertion device and an insertion set according to one embodiment.

FIG. 1 illustrates an embodiment of an insertion device 100 for an infusion device 102, such as infusion set. Further details regarding some exemplifying infusion devices, including infusion sets, are provided in United States Patent Application Publication Nos. 2005/0107743 and 2007/0185441, both of which are hereby incorporated by reference herein in their entireties. There are many different types of infusion devices, such as infusion sets, that may be inserted using insertion devices, and the foregoing publications are provided merely to illustrate some infusion devices that can be used with or adapted to be used with the insertion devices described herein.

Referring to FIG. 1, the insertion device 100 can comprise an actuator 104, a sleeve 106, an insertion spring 108, a needle hub 110, a needle 112, a retraction spring 114, a shuttle or carriage 116, a protective cap 118, and a cover 120. The infusion device 102 can be an infusion set, and can comprise a base 122 and a tubing set 124. The base 122 can comprise a soft cannula 264 and an adhesive sheet 266. The tubing set can comprise an infusion cap 240, a length of tubing 250, and a connector 254 (see FIG. 13). In some embodiments, the infusion device 102 can be packaged within the insertion device 100.

Figure 2:
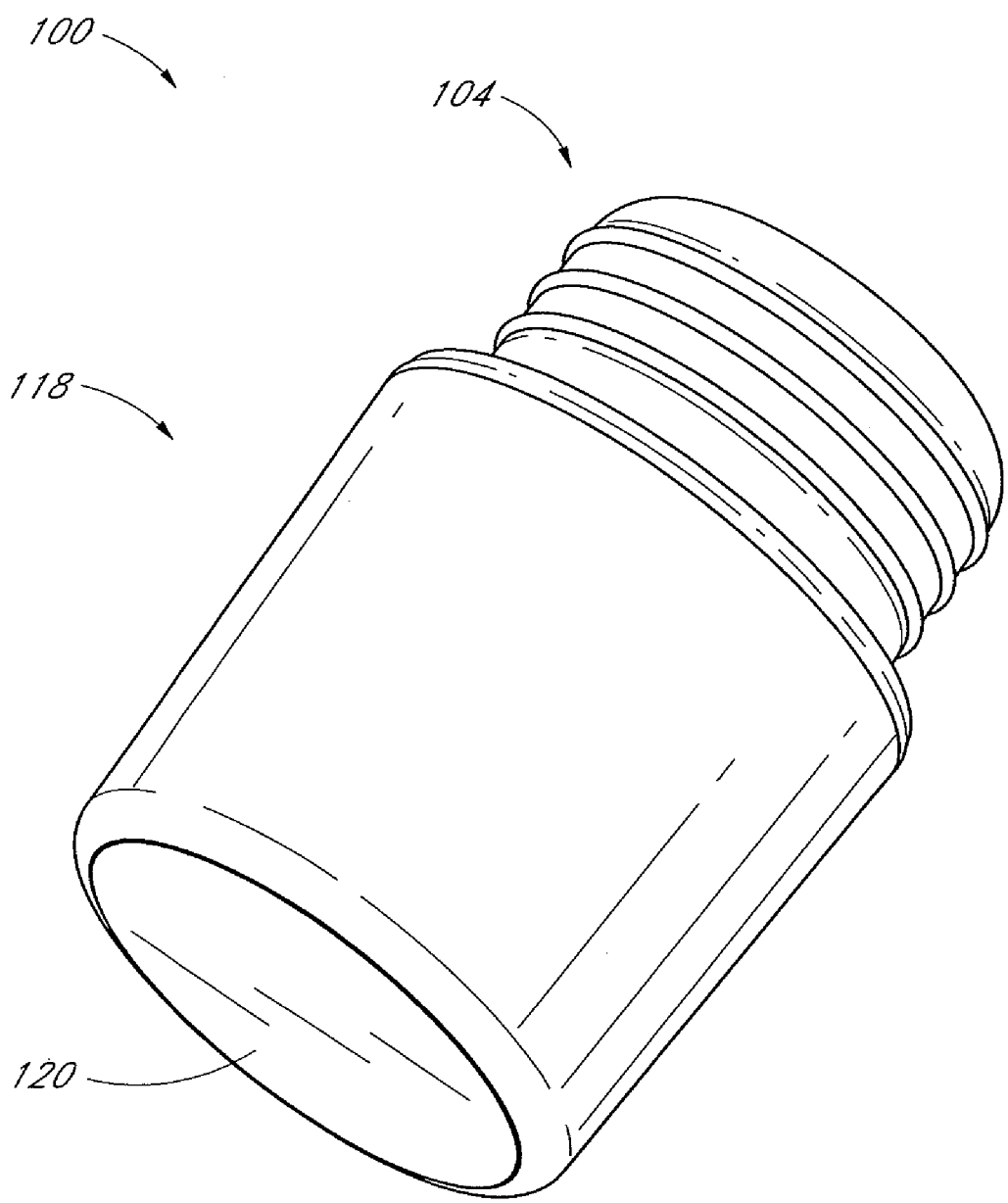
FIG. 2 is an assembled perspective view of the insertion device of FIG. 1.
Figure 3:
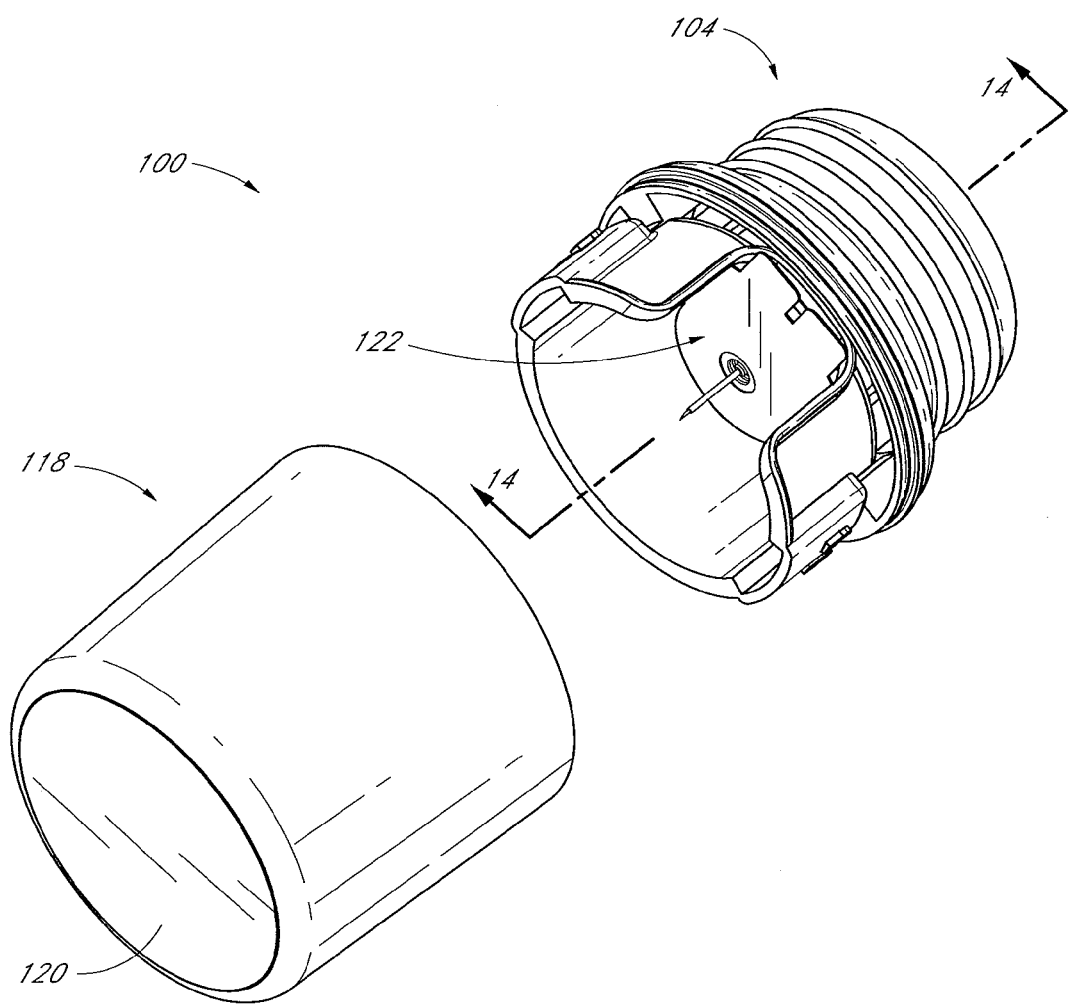
FIG. 3 illustrates a protective cap removed from an actuator of the insertion device of FIG. 1.

FIG. 2 illustrates the insertion device 100 in an assembled state with the protective cap 118 engaged with the actuator 104. The protective cap 118 can be removed from the actuator 104, as shown in FIG. 3, in preparation for insertion of the base 122. In some embodiments, the insertion device 100 may omit the cap 118.

Figure 4:
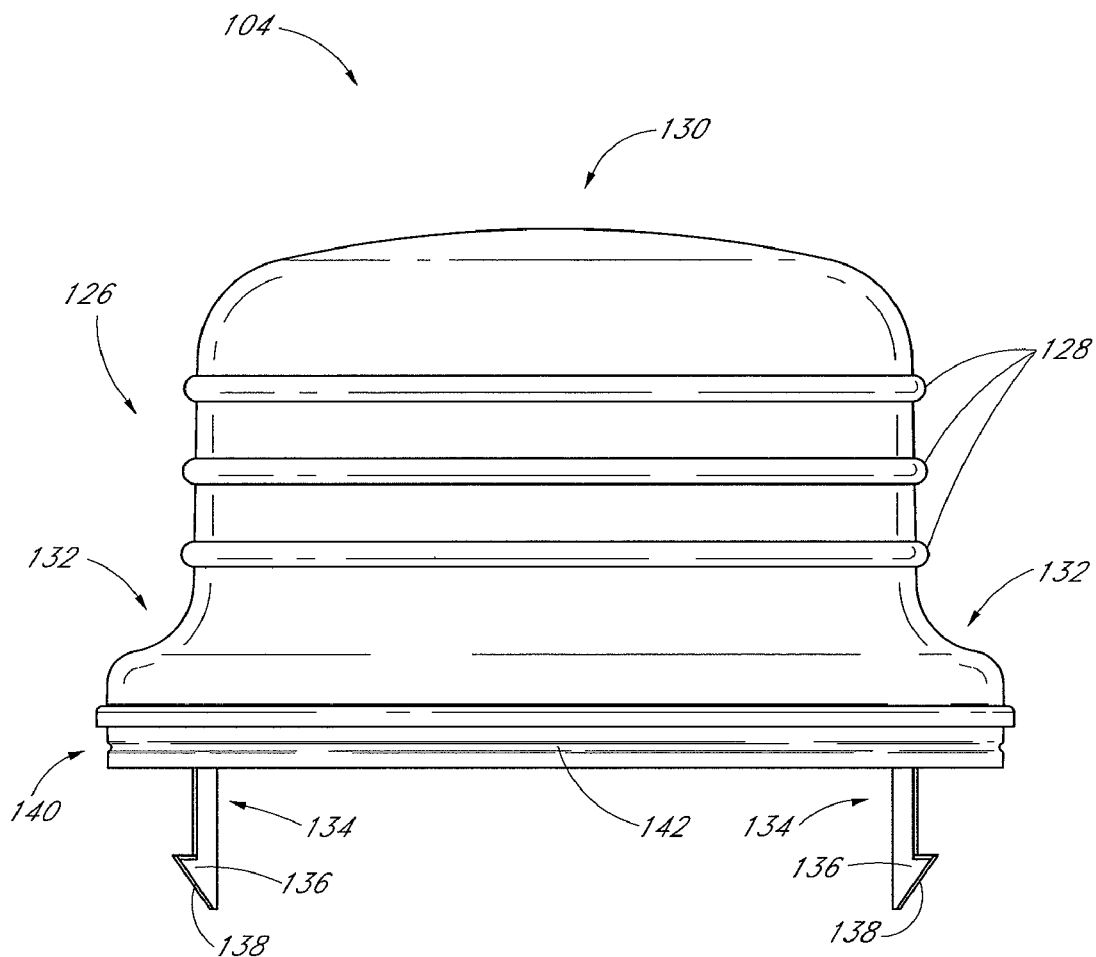
FIG. 4 is a side view of the actuator of the insertion device of FIG. 1.

Referring to FIG. 4, the actuator 104 can include one or more gripping surfaces 126, one or more pushing surfaces 130, one or more arms 134 having feet 136, and a coupling region 140. In some embodiments, the actuator 104 can be made of a rigid plastic, such as ABS (acrylonitrile butadiene styrene), polycarbonate, polyethylene, or PET (polyethylene terephthalate).

The gripping surface 126 can extend entirely or partially around the circumference of the actuator 104 or may alternatively be located on opposite sides of the actuator 104 or otherwise spaced on the actuator 104. The gripping surface 126 preferably has a dimension, such as an external diameter, that is sufficiently large to facilitate easy grasping by diabetics who have lost dexterity and strength due to diabetic neuropathy. In embodiments having multiple gripping surfaces 126, the gripping surfaces can be spaced apart by a distance for facilitate easy grasping. The gripping surface(s) 126 can also have sufficient surface area and be positioned to allow a user to hold the actuator 104 at the gripping surface(s) 126 using the middle section of a user's fingers and/or palm.

In some embodiments, the gripping surface 126 can include a plurality of ridges or other surface elements 128. Surface elements 128 can increase friction or interface between a user's fingers and the actuator 104 to improve the user's ability to securely hold the actuator 104. For example, the surface elements 128 can comprise one or more of texturing, dimples, bumps, grooves, or other surface shapes. The surface elements 128 can be integrally formed with one or more other portions of the actuator 104, or may be separately formed and attached by mechanical coupling, such as by interference fit, or by any known bonding technique, such as adhesives.

The pushing surfaces 130, 132 of the actuator 104 can comprise one or more upper pushing surfaces 130 and/or one or more lower pushing surfaces 132 that can be sized and positioned to be contacted by a user's fingers and/or palm. For example, the upper pushing surface 130 can be configured to be contacted primarily by a user's palm, while lower pushing surfaces 132 can be configured to be contacted primarily by a user's fingers. In the embodiment of the actuator 104 that is illustrated in FIG. 4, the upper pushing surface 130 is generally convexly domed and the lower pushing surface 132 is generally concave.

With continued reference to FIG. 4, the actuator can comprise one or more arms 134 which can have feet 136. The feet 136 may be located at or near a terminal end of arms 134. The feet can include a cam surface 138 and may face outwardly, as illustrated in FIG. 4, inwardly or circumferentially or in other directions. In some embodiments, the actuator 104 may omit the arms, feet, and cam surfaces. In some embodiments, the actuator 104 can comprise other features.

The coupling region 140 may facilitate secure attachment of the actuator 104 with the protective cap 118 (see FIGS. 1 and 2). The coupling region 140 can comprise a groove 142 which can securely engage a complementary structure of the protective cap 118, while also allowing easy removal of the protective cap 118 from the actuator 104. In some embodiments, the coupling region 140 can additionally or alternatively comprise a ridge which can securely engage a complementary structure of the protective cap 118, while also allowing easy removal of the protective cap 118 from the actuator 104.

Figure 5:
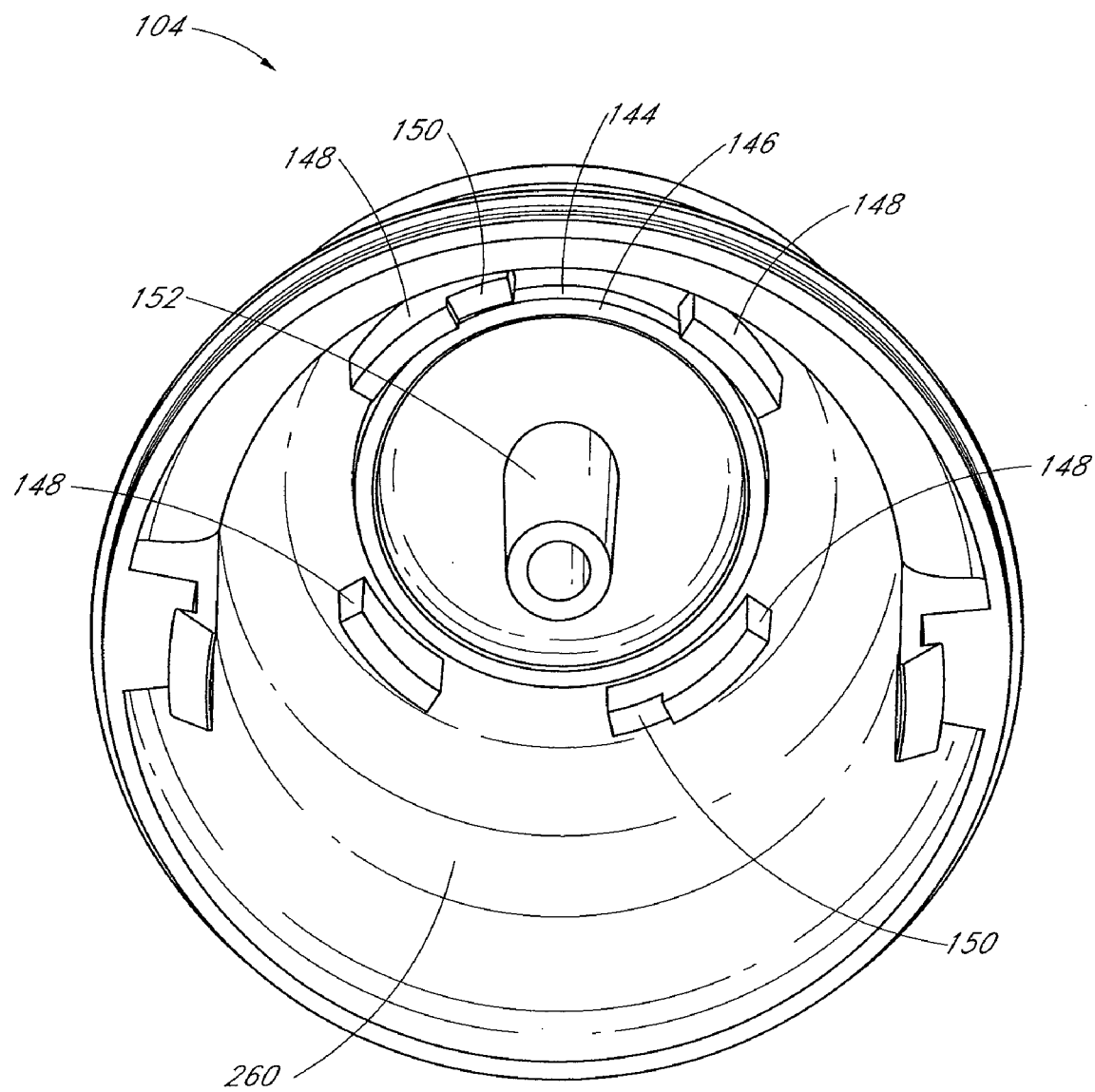
FIG. 5 is a lower perspective view of the actuator of FIG. 5.

Referring to FIG. 5, the actuator 104 can comprise a number of features in an interior of the actuator 104. For example, the actuator 104 can comprise one or more displacement members 144, one or more guideposts 148, and a travel-limiting member 152. Some or all of the displacement members 144, the guideposts 148, and the travel-limiting member 152 can extend downwardly from the underside of the actuator 104. The displacement member 144 can include an engagement surface 146. One or more of the guideposts 148 may include a stop surface 150. The travel-limiting member 152 may be cylindrical, or may have other configurations, such as square, triangular, frustoconical, or actuate.

Figure 6:
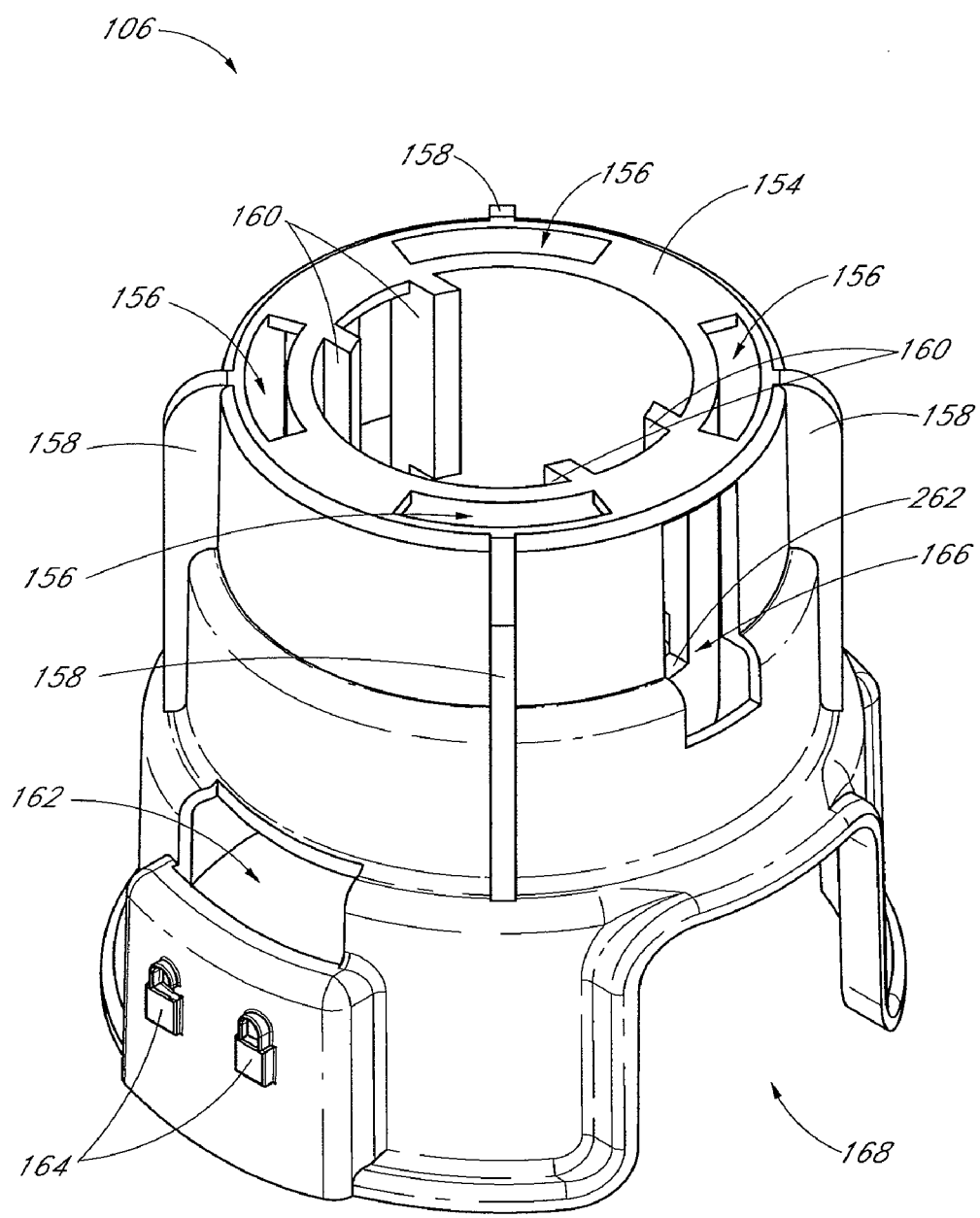
FIG. 6 is an upper perspective view of the sleeve of the insertion device of FIG. 1.

Referring to FIG. 6, the sleeve 106 can comprise an upper surface 154. The upper surface 154 can include one or more apertures 156 that are sized and positioned to cooperate with the guideposts 148 of the actuator 104. Alternatively, the apertures 156 can be formed in a surface of the sleeve other than the upper surface 154. In some embodiments, the apertures 156 can comprise recesses formed in the sleeve 106, such as in the upper surface 154, in a side surface, or both.

The sleeve 106 can comprise one or more external guide rails 158 and/or one or more internal guide rails 160. The external guide rails 158 are preferably sized and configured to cooperate with one or more interior surfaces of the actuator 104, such as interior surface 260 (see FIG. 5). For example, the external guide rails 158 can slidingly engage the interior surface 260 of the actuator 104 to cause the actuator 104 and the sleeve 106 to move along a generally straight path with respect to one another. The external guide rails 158 can additionally or alternatively cooperate with one or more interior surfaces of the actuator 104 to allow the cap 104 and the sleeve 106 to rotate with respect to each other. The external guide rails 158 may extend generally linearly (e.g., straight), as shown in FIG. 6, though the external guide rails 158 may also have other configurations.

The internal guide rails 160 can be sized and configured to cooperate with appropriate structures of the shuttle 116, discussed below. The internal guide rails 160 can extend longitudinally, as shown on FIG. 6, or may have other configurations. In some embodiments, the internal guide rails 160 are arranged in pairs to define a channel therebetween.

With continued reference to FIG. 6, the sleeve 106 can also comprise a recess 168. The recess 168 can permit one or more portions of the infusion device 102 to extend therethrough (see FIGS. 14 and 17).

Referring again to FIG. 6, the sleeve 106 can comprise one or more apertures 166 that can be used to facilitate molding internal features of the sleeve 106.

The sleeve 106 can also comprise a stop ledge 262, the purpose of which is described further below in connection with FIGS. 14-17.

The sleeve 106 can comprise one or more apertures 162 that are configured to permit the arms 134 of the actuator 104 (see FIG. 4) to extend therethrough. The aperture 162 can have a width that allows the arm 134 to move within the aperture 162 as the actuator 104 is rotated with respect to sleeve 106 between a locked position and an unlocked position. When such embodiments are in the locked position, the stop surfaces 150 of the actuator 104 can be positioned over the upper surface 154 of the sleeve 106 to prevent movement of the actuator 104 relative to the sleeve 106 toward the skin.

When such embodiments are in the unlocked position, the stop surfaces 150 are aligned with the apertures 156 such that the guideposts, including the stop surfaces, are allowed to advance through the apertures 156. The sleeve 106 can also comprise indicia 164 to indicate whether the actuator 104 and sleeve 106 are in the unlocked or locked position.

Figure 7:
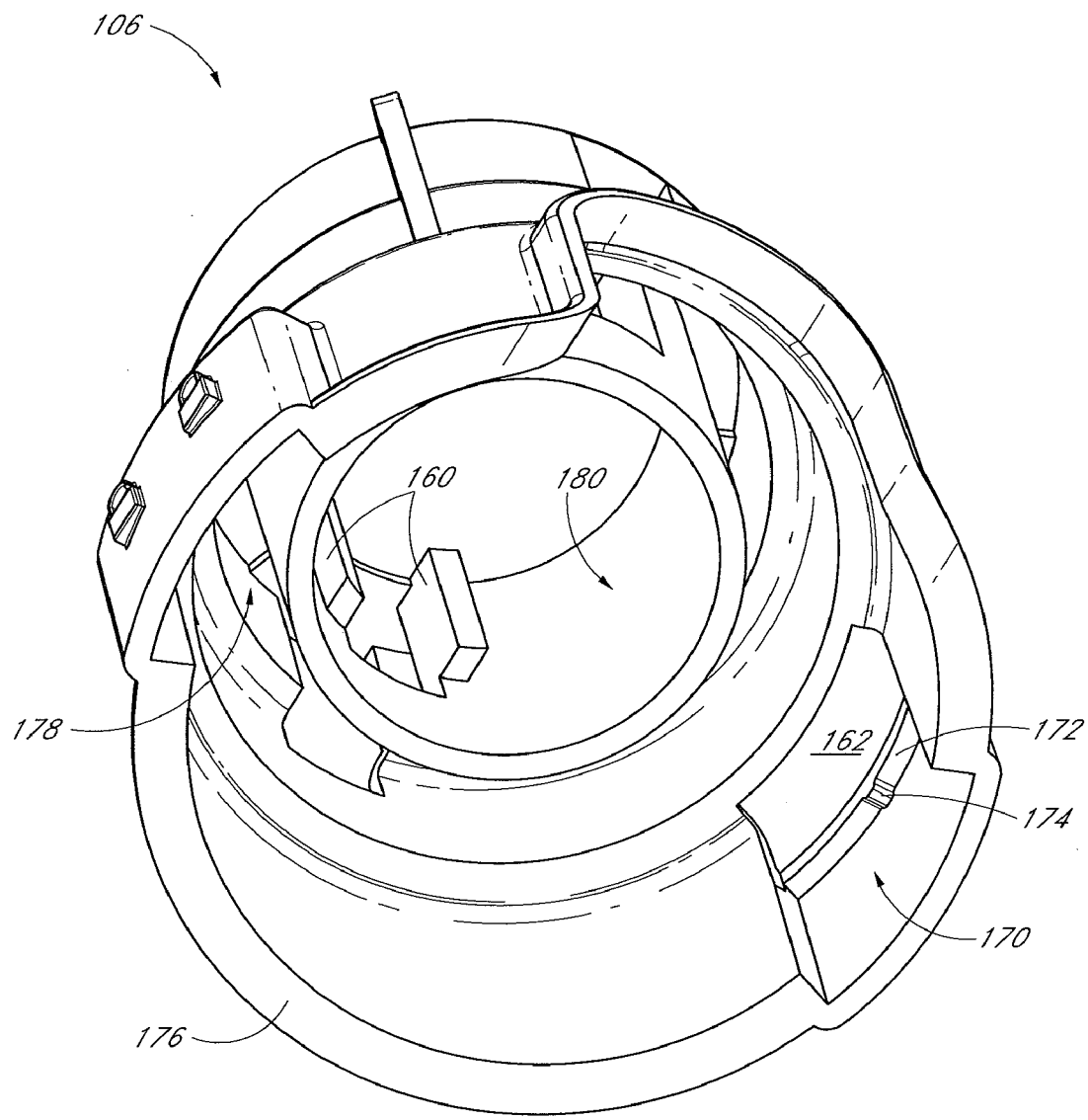
FIG. 7 is a lower perspective view of the sleeve of FIG. 6.

Referring to FIG. 7, the sleeve 106 can comprise a recess 170 in which the one or more feet 136 of the actuator 134 may move. The recess 170 can be bounded on one side by a shoulder 172 that is configured to engage the one or more feet 136 of the actuator 104. The shoulder 172 can comprise a protrusion 174 to prevent unintentional rotation of the actuator 104 with respect to sleeve 106 between the locked position and the unlocked position. The protrusion 174 can also provide tactile feedback to a user when the actuator 104 is moved with respect to the sleeve 106 between the locked position and the unlocked position.

The sleeve 106 can also comprise a lower surface 176. The lower surface 176 can be configured to provide stable contact with a person's skin during placement of the base 122 of the infusion device 102 into the person's skin. The lower surface 176 can be continuous, as illustrated in FIG. 7, or segmented.

In some embodiments, the sleeve 106 can comprise a recess 178 (see, e.g., FIGS. 15 and 16) to receive all or a portion of the insertion spring 108 therein.

With continued reference to FIG. 7, in some embodiments, the sleeve 106 can comprise a cam surface 180. The cam surface 180 can be cylindrical, as illustrated in FIG. 7, or have other configurations. For example, the cam surface 180 can have a generally circular cross-section, as illustrated in FIG. 7, or can have other cross-sectional shapes such as polygonal. The cam surface 180 can form a closed loop as shown in FIG. 7, or may not form a closed loop, but instead comprise one or more longitudinal cam surfaces.

In some embodiments, the sleeve 106 can be made of a rigid plastic, such as ABS, polycarbonate, polyethylene, or PET.

Figure 8:
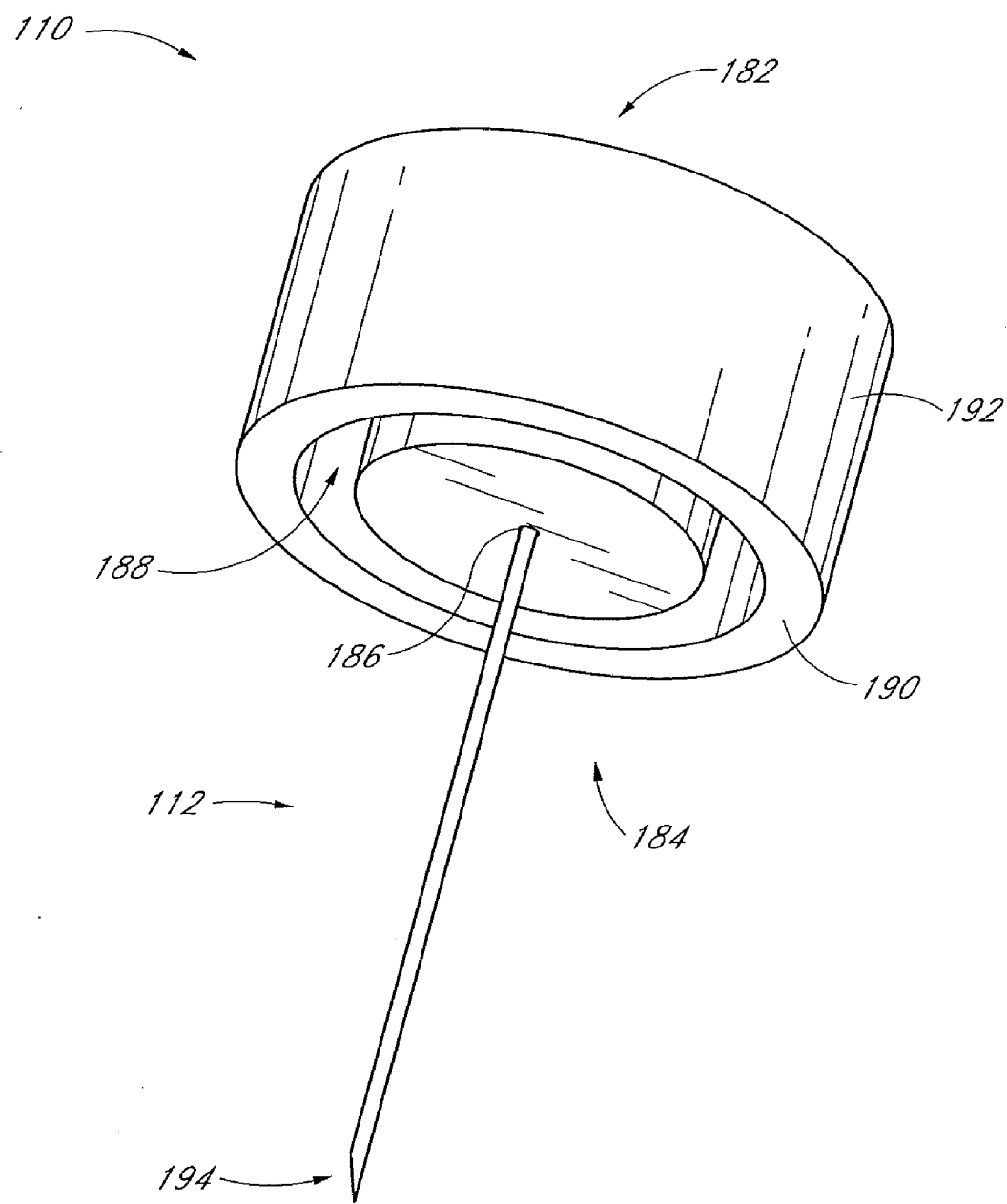
FIG. 8 is a lower perspective view of a needle and needle hub of the insertion device of FIG. 1.

Referring to FIG. 8, the needle hub 110 can comprise an upper side 182 and a lower side 184. The lower side 184 can comprise a needle-mounting aperture 186 and a recess 188. The recess 188 can be configured to receive all or a portion of the retraction spring 114 (see FIGS. 1 and 14-17). The needle hub can also include one or more engagement surfaces 190 and a follower surface 192. In some embodiments, the needle hub 110 can be made of a rigid plastic, such as ABS, polycarbonate, polyethylene, or PET. As shown in FIGS. 14-17, a horizontal cross-sectional area of the needle hub 100 can be constant between the retracted and advanced positions of the hub.

The needle 112 can be inserted into and fixed within the needle-mounting aperture 186 of the needle hub 110. The needle 112 can be fixed to the needle hub 110 by any suitable adhesive, such as a solvent adhesive. The needle 112 can include a beveled end 194. In some embodiments, the needle 112 can be made of a suitable metal, such as stainless steel.

Figure 9:
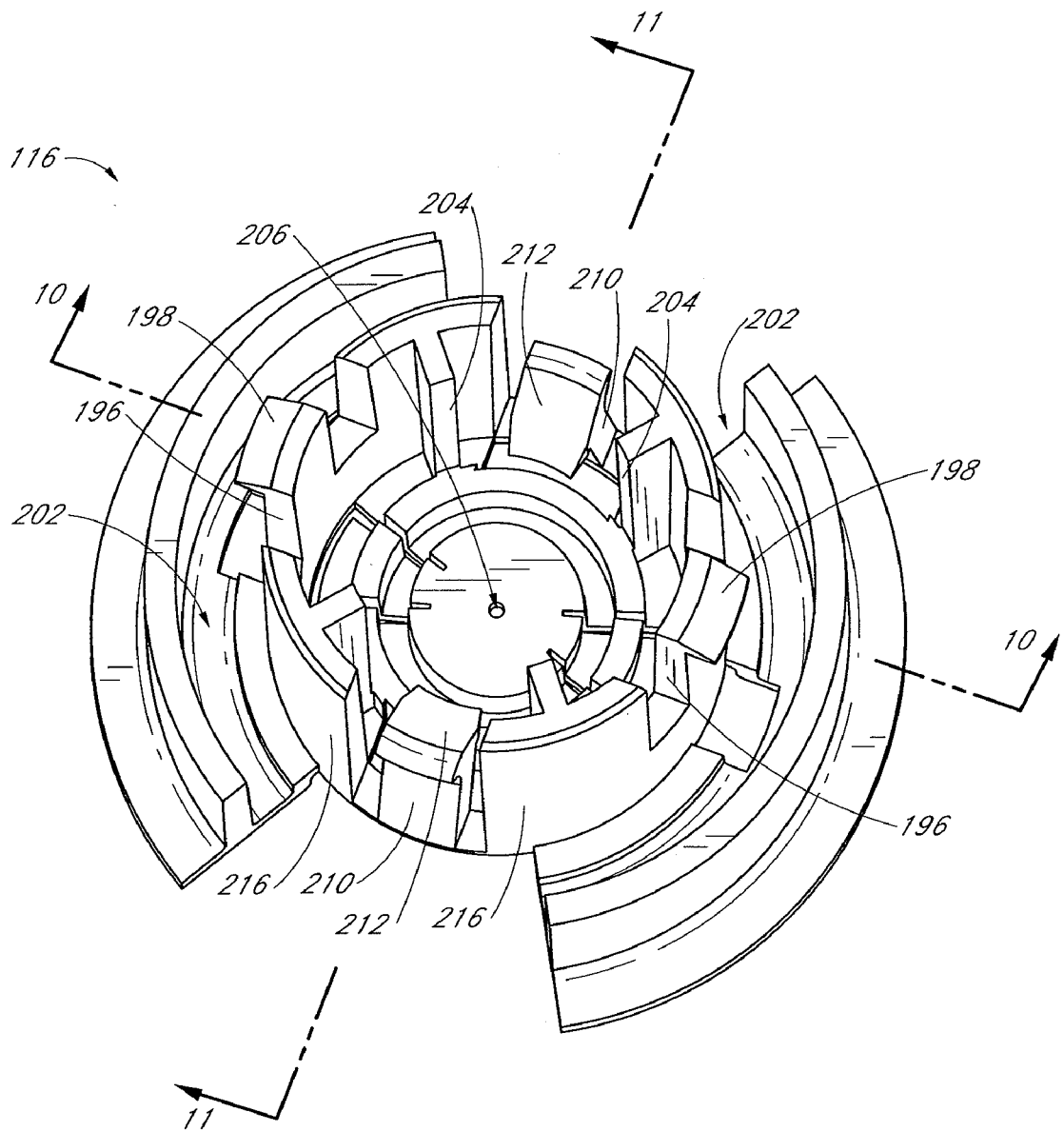
FIG. 9 is an upper perspective view of a shuttle of the insertion device of FIG. 1.
Figure 10:
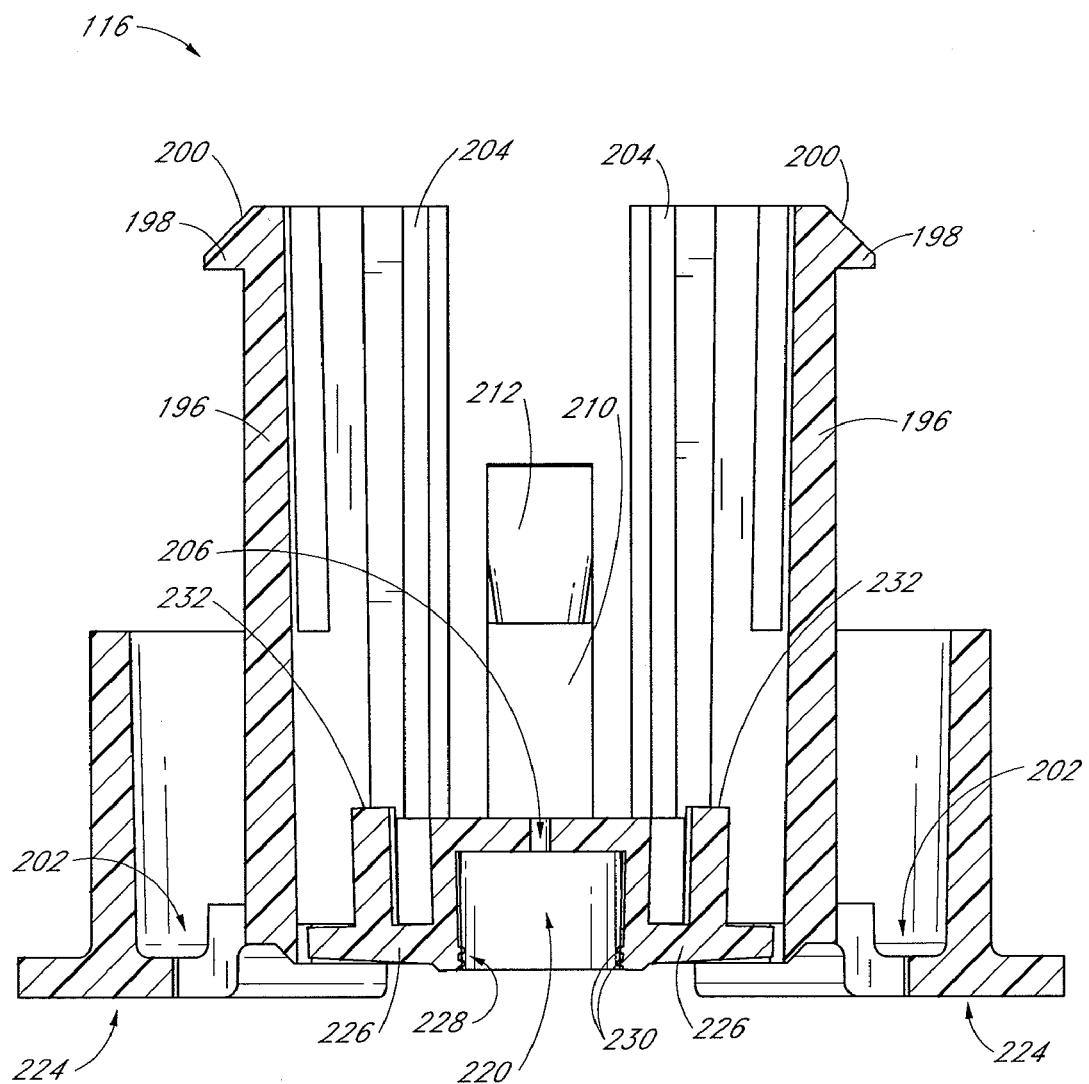
FIG. 10 is a cross-sectional view of the shuttle of FIG. 9, taken along line 10-10 shown in FIG. 9.
Figure 11:
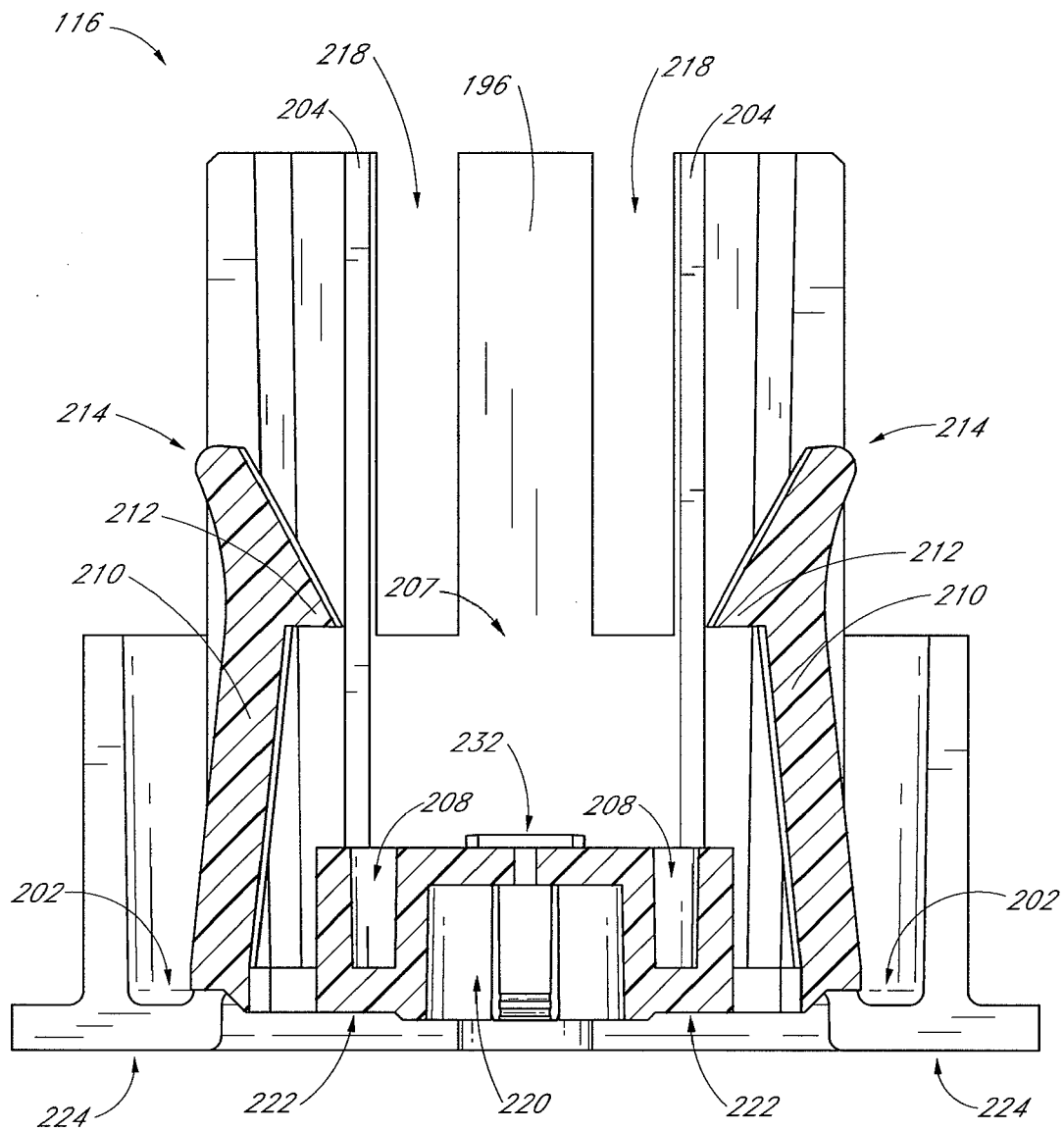
FIG. 11 is a cross-sectional view of the shuttle of FIGS. 9 and 10, taken along line 11-11 shown in FIG. 9.

Referring to FIGS. 9-11, the shuttle 116 can include recesses 202 that are configured to receive at least a portion of the insertion spring 108 (see FIGS. 14-17). The insertion spring 108 can engage the sleeve 106, and the insertion spring 108 can bias the shuttle 116 from the sleeve 106. The guideposts 148 can extend through the apertures 156 in the sleeve 106 (FIG. 6), and the insertion spring can engage the guideposts 148 to bias the actuator from the shuttle 116 (see FIGS. 14-15).

The shuttle 116 can include one or more sleeve-engaging arms 196, each having a sleeve-engaging foot 198. The sleeve-engaging arms 196 of the shuttle 116 can be biased so that the sleeve-engaging feet 198 rest upon the upper surface 154 of the sleeve 106 to maintaining the insertion spring 108 in a compressed state (see FIG. 14).

Figure 14:
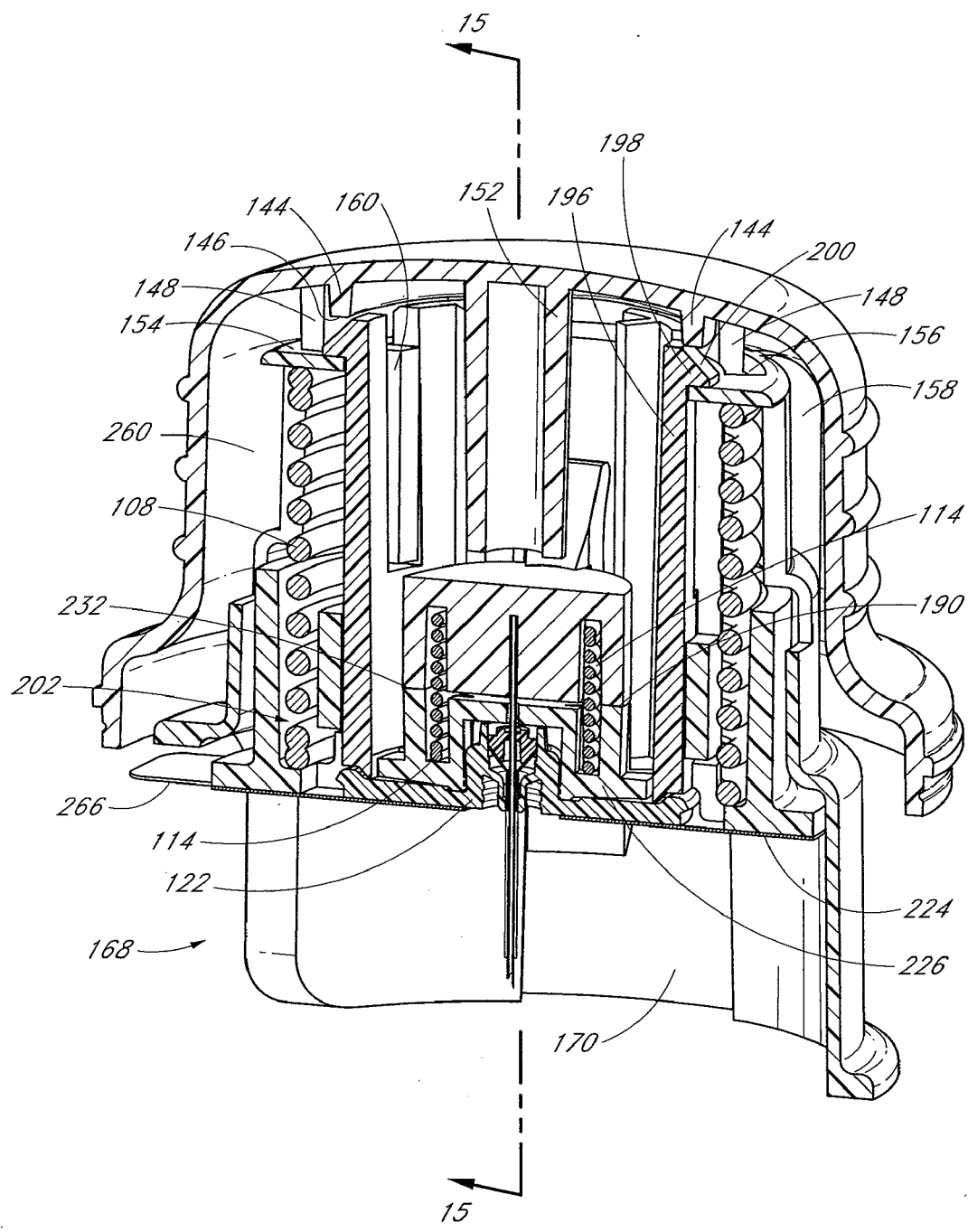
FIG. 14 is a cross-sectional view of the insertion device of FIG. 1 before actuation, taken along line 14-14 shown in FIG. 3.
Figure 15:
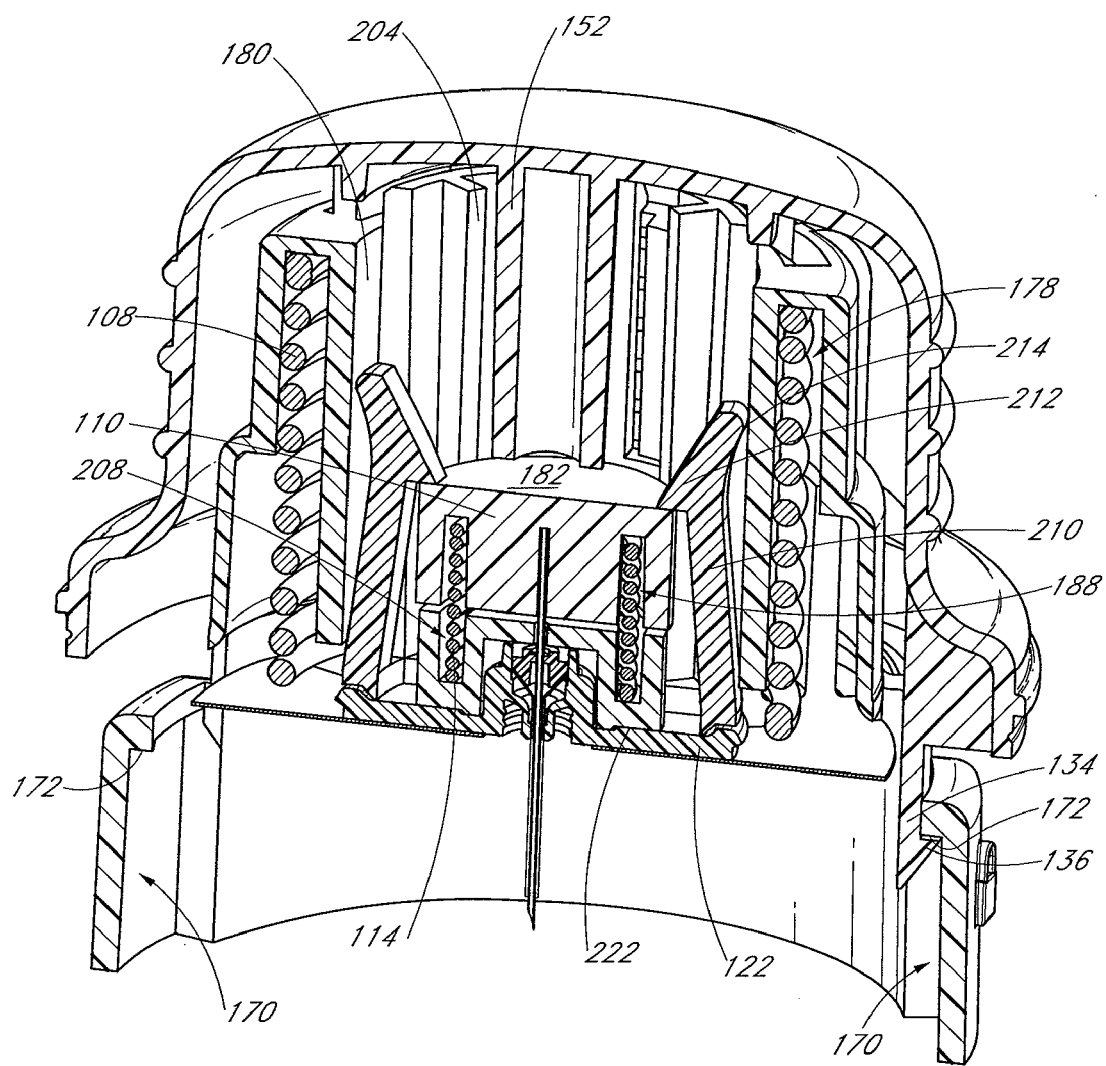
FIG. 15 is another cross-sectional view of the insertion device in FIG. 1 before actuation, taken along line 15-15 shown in FIG. 14.

The sleeve-engaging feet 198 and upper surface 154 are preferably configured to align with the displacement member 144 of the actuator 144 so that the engagement surface 146 of the displacement member 144 aligns with cam surfaces 200 of the sleeve-engaging feet 198. Thus, movement of the displacement member 144 against the feet 198 can cause the feet 198 to disengage from the upper surface 154 of the sleeve 106. The cam surfaces 200 of the sleeve-engaging feet 198 can be beveled, as shown in FIGS. 9-10 and 14, or alternatively the engagement surface 146 can be beveled.

The shuttle 116 can be configured to accommodate the needle hub 110 and needle 112. For example, the shuttle 116 can comprise one or more cam surfaces 204 configured to cooperate with the follower surface 192 of the needle hub 110 to orient the needle hub 110 while permitting sliding movement of the needle hub 110 relative to the shuttle 116. The shuttle 116 can also comprise a needle aperture 206 to permit the needle 110 to extend therethrough.

Referring to FIG. 11, the shuttle 116 can comprise one or more recesses 208 to receive at least a portion of the retraction spring 114. The retraction spring also can engage the needle hub 110, at the recess 188 for example, and the retraction spring 114 can bias the needle hub 110 from the shuttle 116 (see FIGS. 14-17).

With continued reference to FIGS. 9-11, the shuttle 116 can include one or more needle-hub-engaging arms 210, each having a needle-hub-engaging foot 212. The needle-hub-engaging arms 210 can be biased away from the needle hub 110 to allow the needle hub 110 to move freely along the guide surfaces 204. The needle hub 110 can be forced toward the shuttle 116 to compress the retraction spring 114 (see FIGS. 14 and 15). The needle-hub-engaging arms 210 can then be forced together so that the needle-hub-engaging feet 212 engage the upper side 182 of the needle hub 110 to restrict movement of the needle hub 110 away from the shuttle 116. As shown in FIG. 11, the needle hub 110 can be positioned in an internal cavity 207 having a horizontal cross-sectional area, and a horizontal cross-sectional area of the needle hub 110 (see FIGS. 14 and 15) can be smaller than a horizontal cross-section of the internal cavity 207. The needle-hub-engaging arms 210 can also comprise a follower surface 214 (see FIG. 11) that cooperates with the cam surface 180 of the sleeve 106 to prevent the needle-hub-engaging arms 210 from spreading apart to release the needle hub 210 (see FIGS. 15 and 16).

Referring to FIG. 9, the shuttle 116 can comprise guide surfaces 216 that are sized in positioned to cooperate with the can surface 180 of the sleeve 106 to orient of the shuttle 116 relative to the sleeve 106 as the shuttle 116 moves away from the sleeve 106 under the force of the insertion spring 108.

Referring to FIG. 11, the shuttle 116 can comprise slots 218 that are sized and configured to cooperate with internal guide rails 160 of the sleeve 106 to inhibit or prevent rotation of the shuttle 116 relative to the sleeve 106 and guide the movement of the sleeve-engaging arms 196 and sleeve-engaging feet 198.

Referring to FIGS. 10 and 11, the shuttle 116 can comprise a recess 220 to receive at least a portion of an infusion device 102. The recess 220 can be positioned such that the needle 112 extends through the needle apertures 206 and through the cannula 264 of the base 122. The shuttle 116 can also comprise additional surfaces such as surfaces 222 and 224, to engage the infusion device 102.

The shuttle 116 can comprise one or more base-retaining arms 226. In some embodiments, the base-retaining arms 226 can extend into the recess 220 to engage the infusion device 102. The arms 226 can include set-engagement surfaces 228 that may include features, such as ribs 230, to frictionally engage the base 122. The set-engagement surfaces 228 can be substantially flat or in other embodiments can be concave or have other shapes. The arms 226 can include surfaces 232 positioned for engagement by the needle hub 110 to force the set-engagement surfaces 228 into contact with the infusion device 102 to prevent the infusion device 102 from unintentional disengagement from the shuttle 116. When the needle-hub-engaging arms 210 of the shuttle 116 hold the needle hub 110 to maintain compression of the retraction spring 114, the engagement surface 190 of the needle hub 110 can press against the engagement surfaces 232 to move the arms 226 and thereby squeeze the infusion device 102 between the set-engagement surfaces 228 within the recess 220.

In some embodiments, the shuttle 116 can be made of a rigid plastic, such as ABS, polycarbonate, polyethylene, or PET. Nonetheless, it can be advantageous for the material from which the shuttle 116 is made to have sufficient memory to properly function as described herein.

Figure 12:
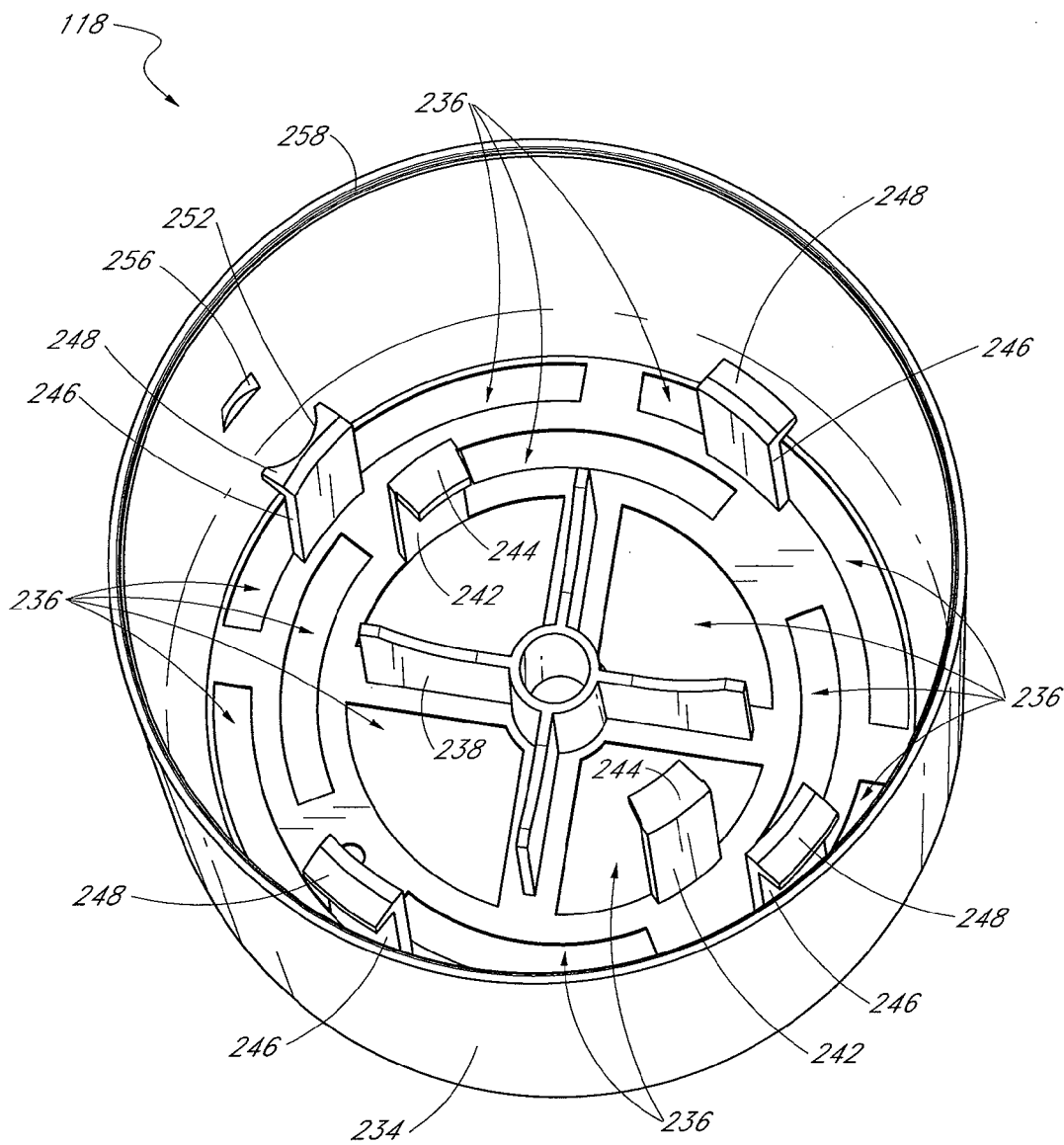
FIG. 12 is an upper perspective view of a protective cap for use with an insertion device.
Figure 13:
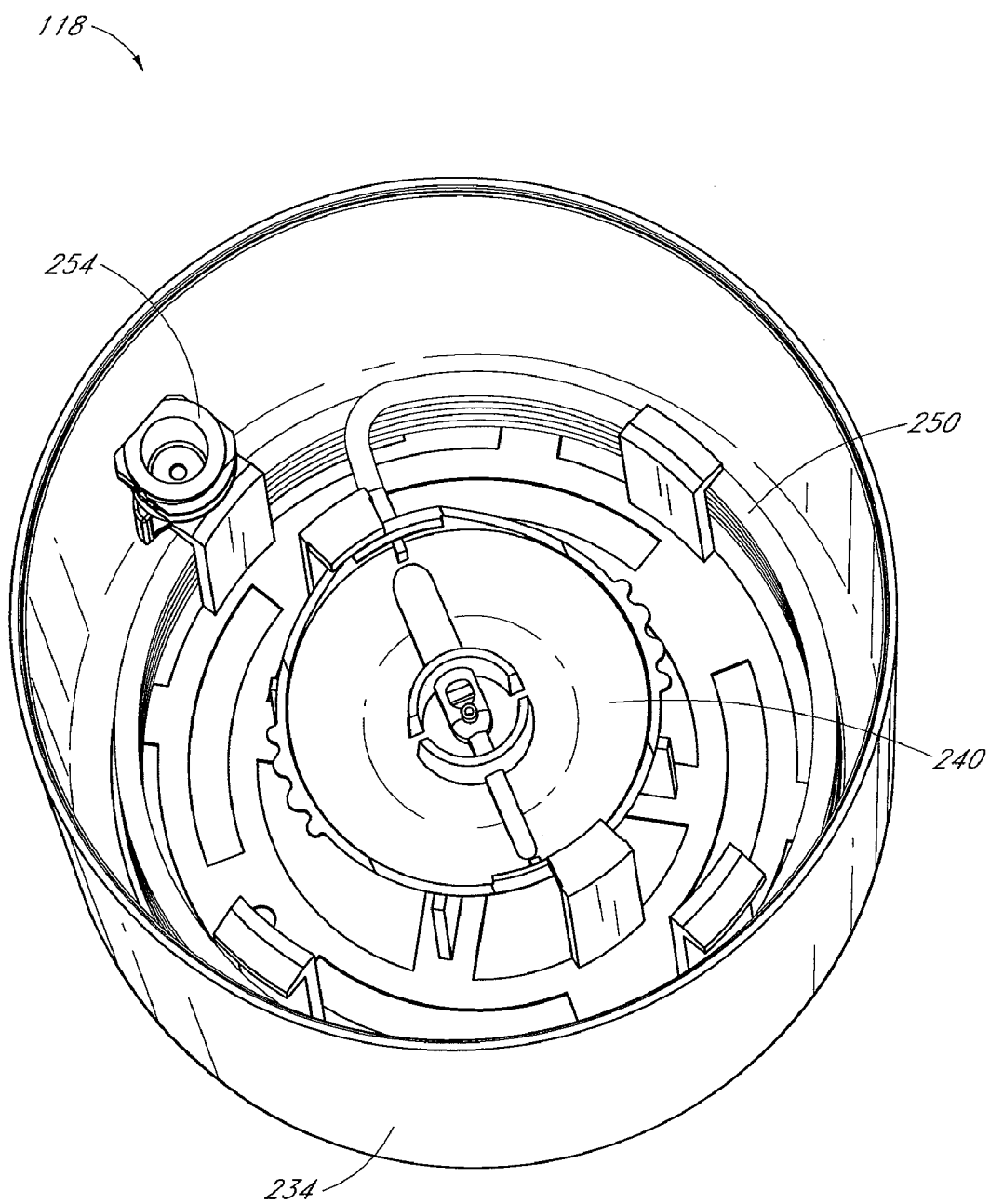
FIG. 13 is an upper perspective view of the protective cap of FIG. 12, showing a portion of an infusion device accommodated therein.

Referring to FIGS. 12 and 13, the protective cap 118 can comprise a cylindrical wall 234 of sufficiently large width, diameter, or length, to accommodate therein the tubing set 124 as illustrated in FIG. 13. The protective cap 118 can include a plurality of apertures 236 to facilitate the sterilization of the insertion device 100 and/or the infusion device 102.

The cover 120 (see FIGS. 1-3) can be applied to the protective cap 118 to cover the apertures 236 before or after sterilization of the insertion device 100 and/or the infusion device 102. In some embodiments, the cover 120 can be made of DuPont Tyvek® or other suitable material.

In some embodiments, the protective cap 118 can comprise one or more structures to receive and retain the tubing set 124 of the infusion device 102. The protective cap 118 can comprise one or more receiving structures 238 to receive the infusion cap 240 and one or more arms 242 having feet 244 to hold the infusion cap 240 securely within the protective cap 118.

The protective cap 118 can include a plurality of arms 246 having feet 248 that are configured to hold the length of tubing 250. One of the arms 246 can also comprise a recess 252 to receive the connector 254. The protective cap 118 can comprise a recess 256 to receive a portion of the connector 254 so that the connector 254 can be held securely between the recess 256 and the arm 246 that includes the recess 252.

The protective cap 118 can comprise a coupling region 258 configured to cooperate with the coupling region 140 of the actuator 104.

In some embodiments, the protective cap 118 can be made of a rigid plastic or a semi-rigid plastic, such as ABS, polycarbonate, polyethylene, or PET. In some embodiments, it may be desirable for the actuator 104 and the protective cap 118 to be made of different materials. For example, the protective cap 118 can be made of a material that is less rigid than the material of the actuator 104 to facilitate operation of the coupling regions 120, 258. Additionally or alternatively, the protective cap 118 can be made of a clear material, such polycarbonate, to facilitate inspection of the infusion device 102 by a manufacturer or user, for example.

The protective cap 118 can advantageously be used for storage and transportation of the tubing set 124. The protective cap 118 can also be used as a sterile environment for the infusion cap 240 while the connector 254 is connected to an infusion pump and the tubing set 124 is primed.

The actuator 104, the sleeve 106, the shuttle 116, and the protective cap 118 can be made of any of a variety of plastics known to those of skill in the art, such as those identified above, or may alternatively be made of metal or other materials. The insertion spring 108 and the retraction spring 114 can be made of plastic, metal, rubber, or other materials. In some embodiments the insertion spring 108 and the retraction spring 114 can be made of steel, such as stainless steel or spring steel. The springs 108 and 114 may have configurations other than that of a helical spring.

The insertion device 100 and infusion device 102 can be packaged together and transported in the assembled state shown in FIG. 2. A label (not shown) may be applied to the side of the protective cap 118 and the actuator 104 to provide instructions to the user and provide a tamper-evident seal to the insertion device 100. The label could be positioned so that the user would need to tear the label before removing the protective cap 118 from the actuator 104, as shown in FIG. 3.

Once the protective cap 118 is removed from the actuator 104, the connector 254 and some or all of the length of tubing 250 are removed from the protective cap 118. The connector 254 is connected to an infusion pump and then the tubing set 124 is primed. The infusion cap 240 is kept within the protective cap 118 to preserve the sterility of the infusion cap 240.

After preparing an injection site on the patient's skin, the user removes protective paper backing, if any, from the adhesive of the base 122. The sleeve 106 is then rotated relative to the actuator 104 from the locked position to the unlocked position and the lower surface 176 of the sleeve 106 is placed on the skin at the injection site.

The actuator 104 can be advanced toward the skin with the external guide rails 158, if present, of the sleeve 106 guiding the actuator 104 as it is advanced. Advancement of the actuator 104 toward the sleeve 106 can disengage or permit disengagement the sleeve-engaging feet 198 of the shuttle 116 from the upper surface 154 of the sleeve 106. For example, referring to FIGS. 14 and 15, the actuator 104 compresses the insertion spring 108 until the engagement surface 146 of the displacement member 144 of the actuator 104 presses against the cam surfaces 200 of the sleeve-engaging feet 198 of the shuttle 116 to force the sleeve-engaging feet 198 off of the upper surface 154 of the sleeve 106 to allow the shuttle 116 to advance within the sleeve 106. The orientation of the shuttle 116 within the sleeve 106 can be preserved as the shuttle 116 advances by cooperation of the internal guide rails 160 in cooperation with the slots 218 of the shuttle 116. Advancement of the shuttle 116 within sleeve 106 can be limited by the engagement of the sleeve-engaging feet 198 against the stop ledge 262 of the sleeve 106 (see FIG. 17).

Figure 16:
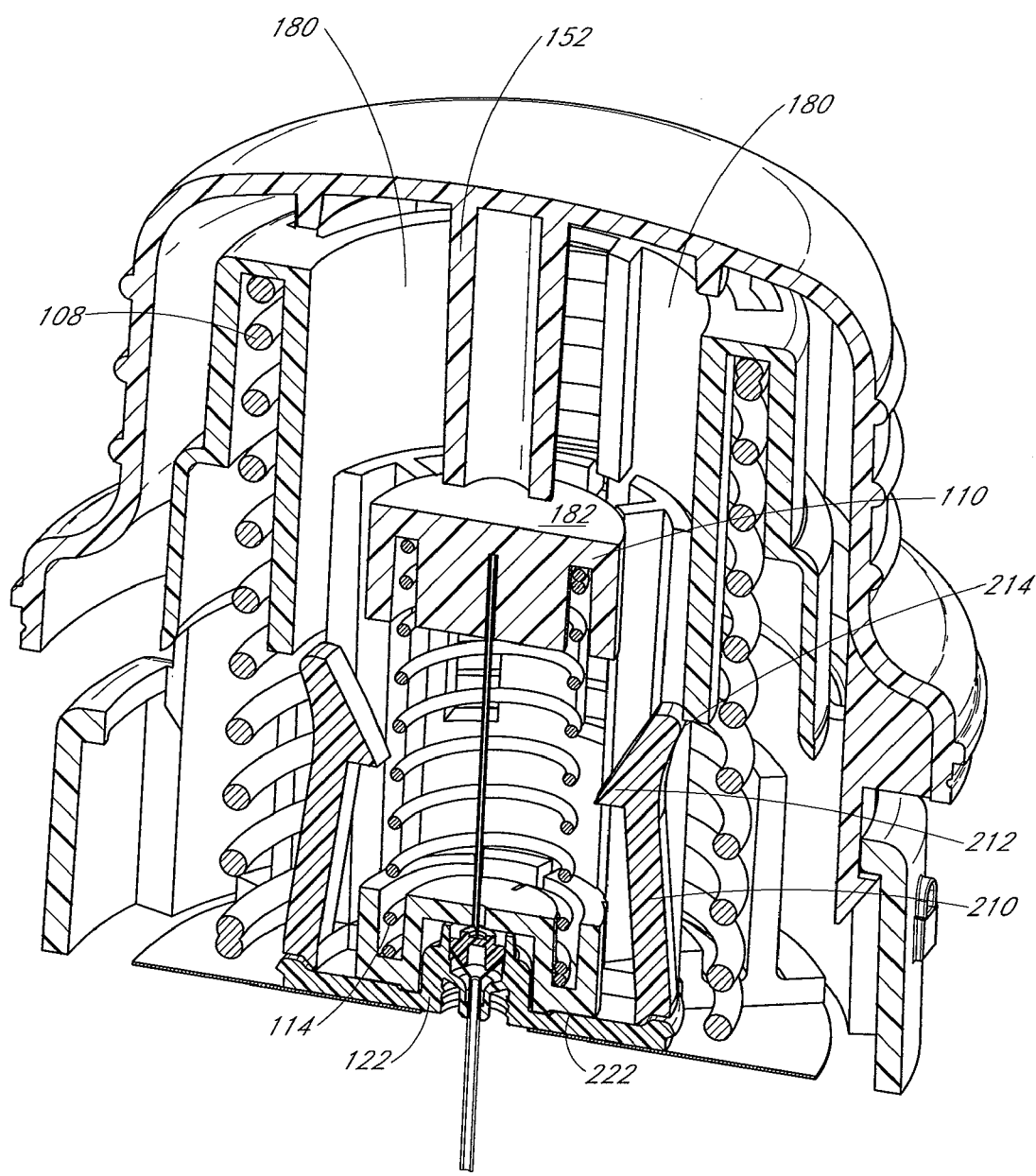
FIG. 16 is a cross-sectional view, similar to FIG. 15, of the insertion device of FIG. 1 after actuation.
Figure 17:
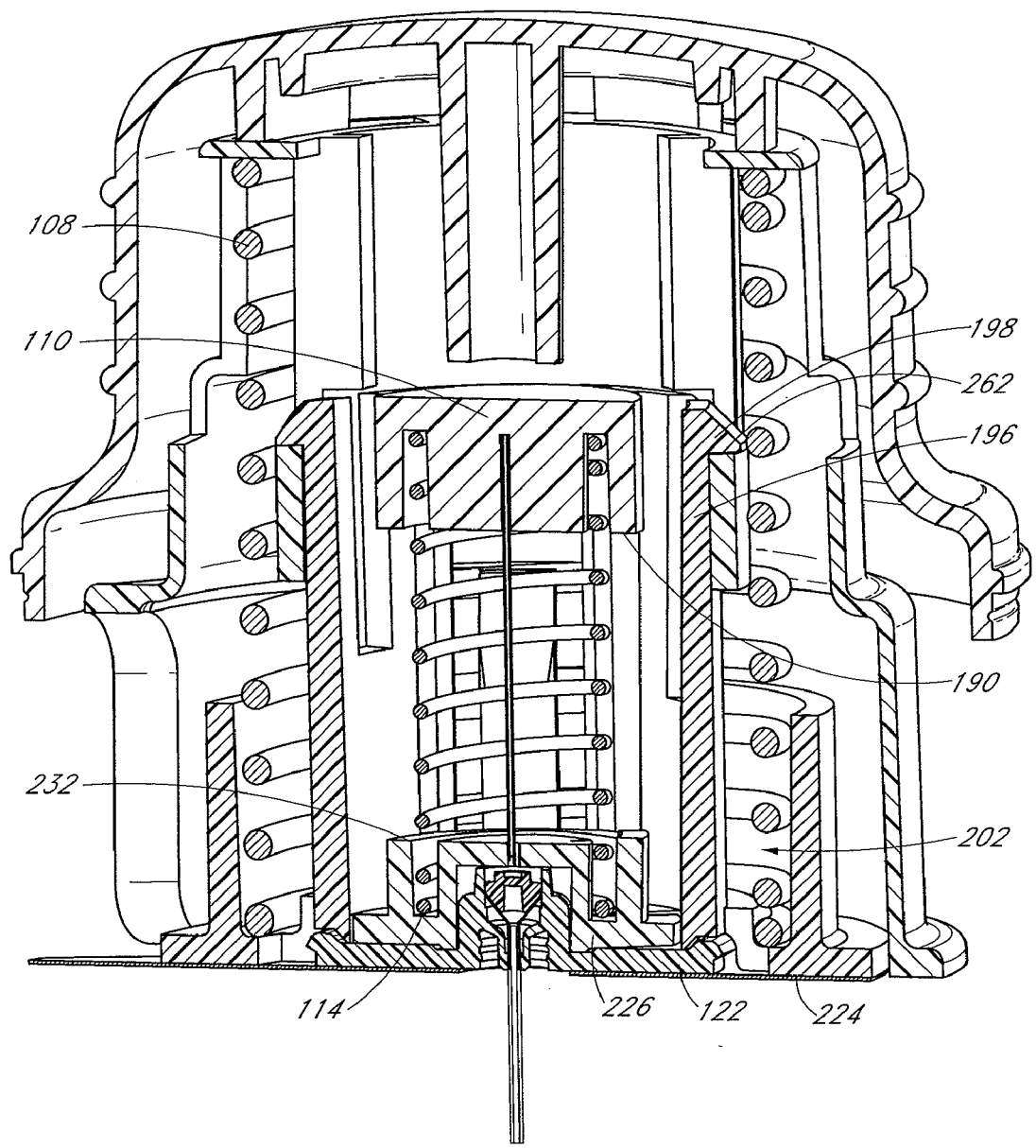
FIG. 17 is another cross-sectional view, similar to FIG. 14, of the insertion device of FIG. 1 after actuation.

Movement of the shuttle 116 from a retracted position toward an advanced position can permit or can cause the hub 110 to move away from the hub 110. For example, as the shuttle 160 approaches or arrives at the end of its range of travel within the sleeve 106, the needle-hub-engaging arms 210 can clear the cam surface 180 of the sleeve 106 to allow the needle-hub-engaging arms 210 to move away from the needle hub 110. Once the needle hub 110 is released by the needle-hub-engaging arms 210, the retraction spring 114 can push the needle hub 110 away from the shuttle 116 to draw the needle 112 within the insertion device 100, as illustrated in FIGS. 16 and 17. The guide surfaces 204 of the shuttle 116 can orient the needle hub 110 as it moves away from the shuttle 116 so that the needle 112 is withdrawn substantially linearly (e.g., straightly) from the skin. Thus, the needle 112 can be protected both before and after insertion of the base 122 to prevent accidental needle sticks. This automatic retraction feature can ensure that the needle 212 is only exposed while the infusion device 102 is being inserted. In some embodiments, the insertion device 100 can be configured to be used only a single time such that the insertion device 100 can be discarded with the needle safely retained therein.

The surfaces 222 and 224 of the shuttle 116 can press the base 122 against the skin. Additionally or alternatively, the surfaces 222 and 224 can inhibit movement of the infusion device 102 away from the skin as the needle 112 is retracted. In embodiments comprising arms 226 (see FIG. 10), once the needle hub 110 moves away from the shuttle 116, pressure can be released from the engagement surface 232 of the arms 226 releasing the set-engagement surfaces 228 from the base 122 so that the base 122 is released from the shuttle 116.

The user may maintain pressure against the cap 104 so that the surfaces 222 and 224 of the shuttle 116 hold a portion of the infusion device 102, such as the base 122, against the skin to ensure good adhesion between the infusion device 102 and the skin. Thereafter, the user may lift the insertion device 100 away from the skin leaving the infusion device 102 against the skin with the cannula extending through the skin.

Once the insertion device 100 is removed from the skin, the protective cap 118 can be engaged with the actuator 104 for safe disposal of the needle 112 within the insertion device 100. However, in some embodiments, the insertion device 100 can be safely disposed with the needle 112 retracted into the insertion device 100 even if the protective cap 118 is omitted or not engaged with the actuator 104.

In some embodiments, the insertion device 100 can be used to insert an infusion set 102 having a rigid infusion cannula 264, such as those described in United States Patent Application Publication No. 2007/0185441, which is hereby incorporated by reference herein in its entirety. Such embodiments of the insertion device 100 may omit the needle 112 if the infusion cannula 264 has sufficient rigidity to pierce skin.

Figure 18:
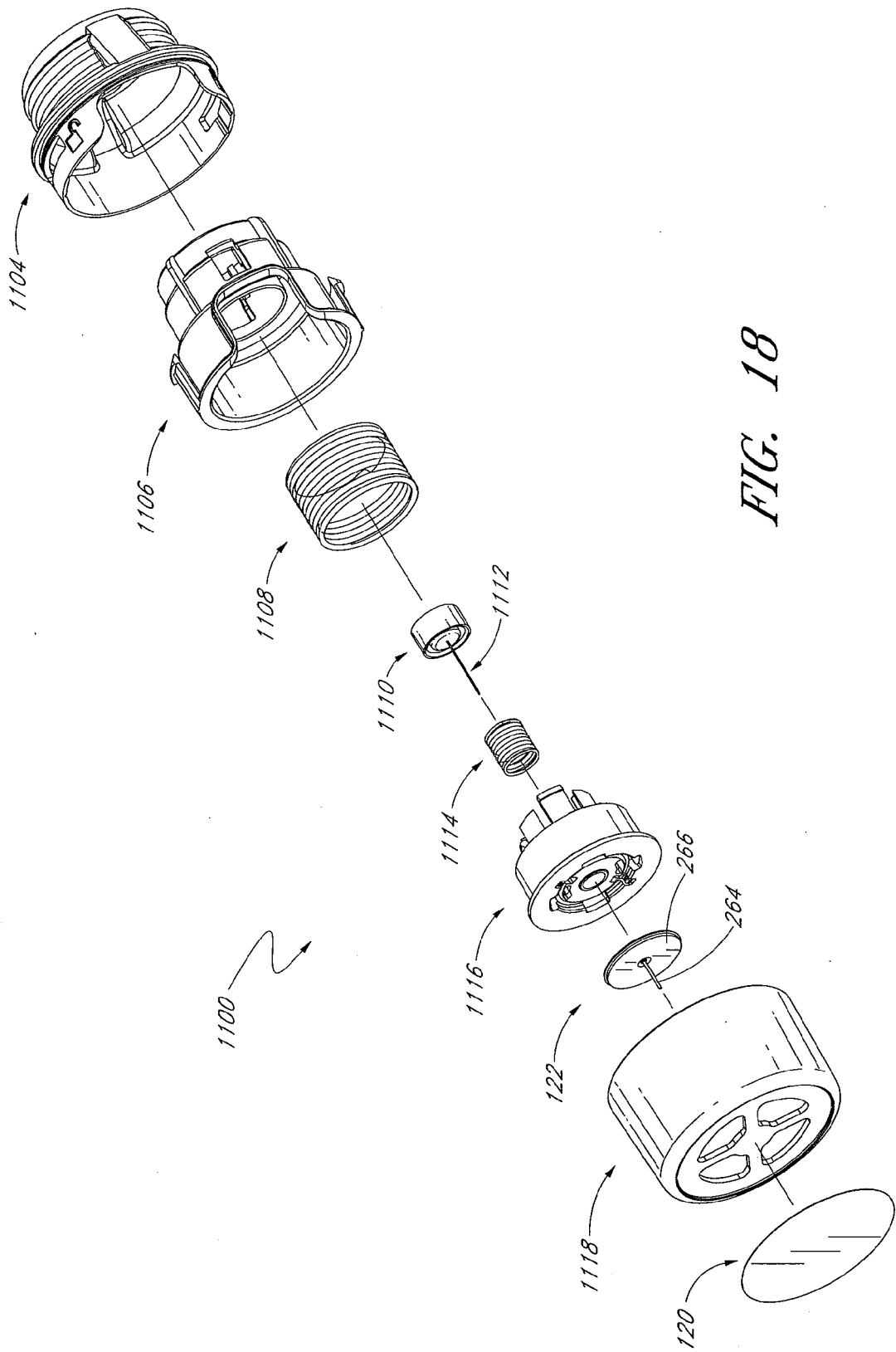
FIG. 18 is an exploded perspective view of an insertion device and an insertion set according to one embodiment.

FIG. 18 illustrates an embodiment of an insertion device 1100 for an infusion device, such as the infusion device 102. The insertion device 1100 is similar in many respects to the insertion device 100. Therefore, similar components of the insertion device 1100 are referenced by the same reference numeral as the corresponding component in the insertion device 100 incremented by one thousand. As with the insertion device 100, the insertion device 1100 can comprise an actuator 1104, a sleeve 1106, an insertion spring 1108, a needle hub 1110, a needle 1112, a retraction spring 1114, a shuttle 1116, a protective cap 1118, and a cover 1120. In some embodiments, the infusion device 102 can be packaged within the insertion device 1100.

The insertion device 1100 can differ from the insertion device 100 in some respects. For example, the actuator 1104 can comprise one or more projections 1107, illustrated in FIGS. 19 and 20. The projections 1107 can extend generally away from one or more gripping surfaces 1126, one or more pushing surfaces 1130, or a combination thereof. The projections 1107 can be spaced substantially evenly around the actuator 1104 or can be otherwise spaced on the actuator 1104. The gripping surfaces 1126 can extend between the projections 1107.

Figure 19:
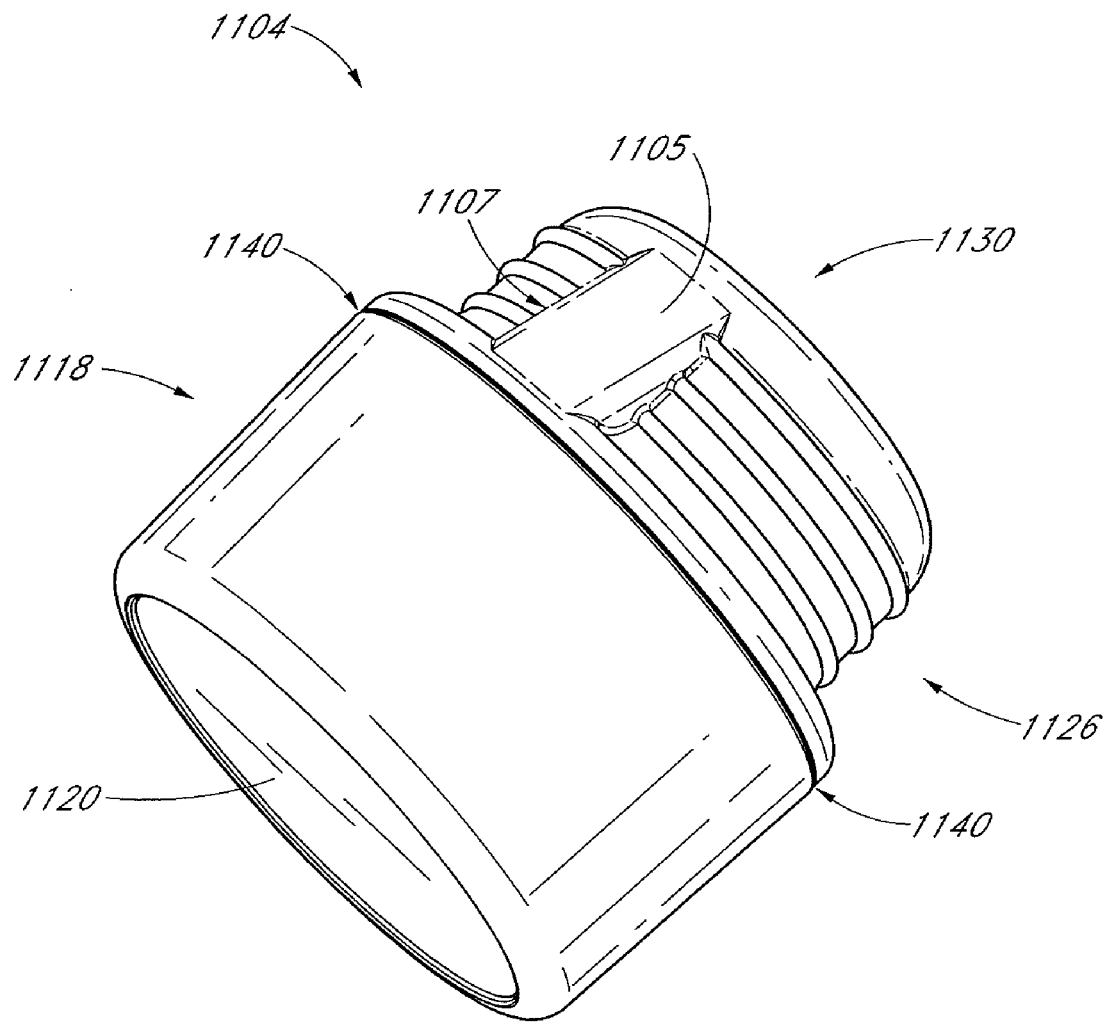
FIG. 19 is an assembled perspective view of the insertion device of FIG. 18.

The projections 1107 can provide one or more advantages. For example, the projections may aid in the removal of a protective wrapping, covering, or other seal or temper-evidencing feature. Insertion devices can be distributed to end-users in a sealed configuration to maintain the insertion devices in a sterile condition. In some embodiments, sterility can be maintained by distributing the insertion device 100, 1100 in an assembled state (FIGS. 3 and 19) and by substantially sealing the coupling region 140, 1140 between the actuator 104, 1104 and the protective cap 118, 1118. In some embodiments, the coupling region 1140 can be wrapped with a layer of plastic or cellophane shrink-wrapping, or a shrink-wrapping formed from any other suitable material. While placing the layer of shrink-wrapping, covering, or other seal or temper-evidencing feature across the coupling region 1140 may help to maintain sterility and can indicate whether tampering has occurred, the removal of such layer may be difficult for some users, particularly for those suffering from diabetic neuropathy because of the associated loss of dexterity. In some embodiments, the projections 1107 can comprise one or more surfaces 1105, as shown in FIG. 19, to facilitate removal of the shrink-wrapping, covering, or other seal or temper-evidencing feature from the coupling region 1140. For example, the shrink-wrapping could be removed by rubbing the surface 1105 against another object, creating a pressure on the shrink-wrapping sufficient to loosen, tear or otherwise remove the shrink wrapping. The surfaces 1105 may also provide a suitable location for provision of a tab, perforation, or other feature to aid a user in removing a protective wrapping, covering, or other seal or temper-evidencing feature. Additionally or alternatively, the projections 1107 may aid manipulation of the actuator 1104 during use or manufacturing by indicating the orientation of the actuator 1104, providing additional surfaces or surfaces for gripping, or both.

Figure 20:
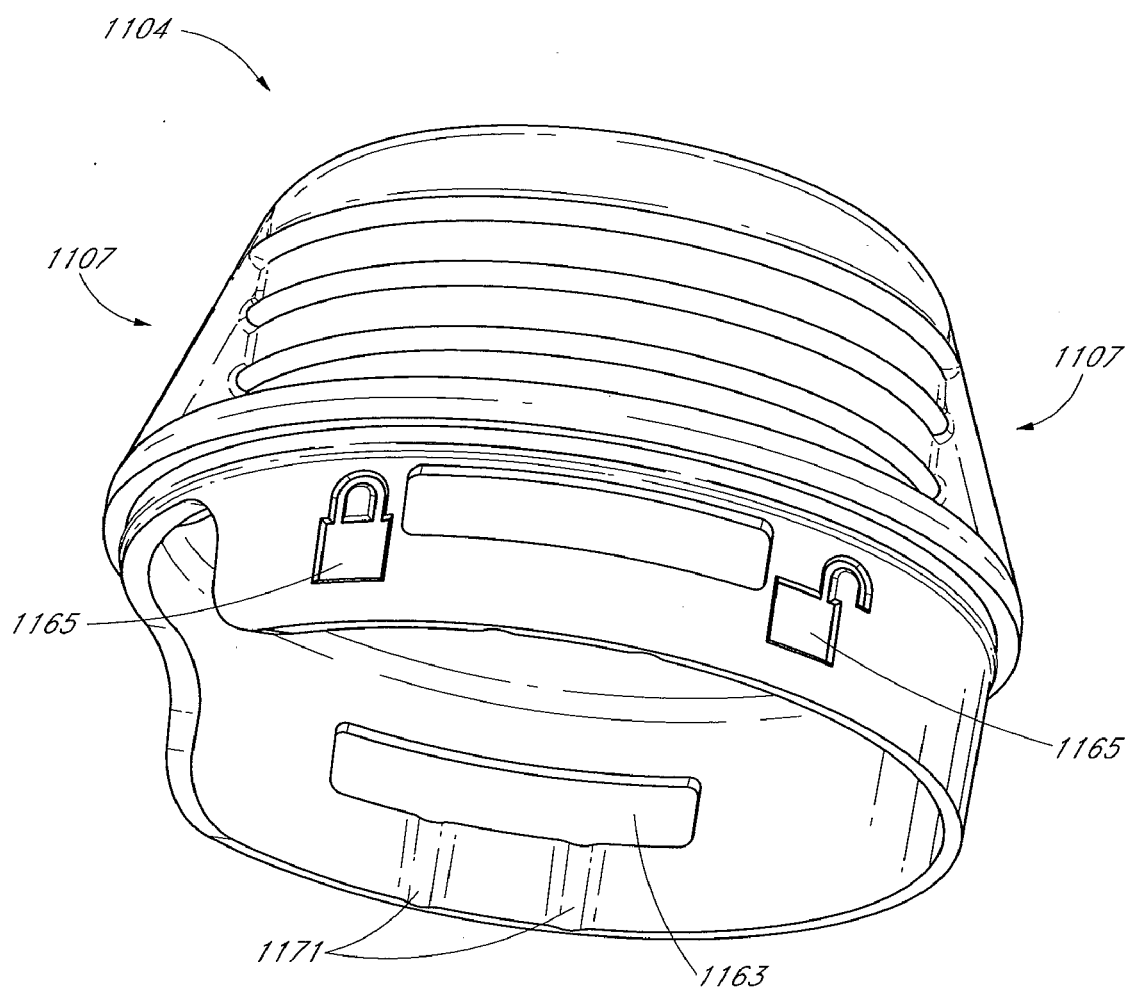
FIG. 20 is a perspective view of an actuator of the insertion device of FIG. 18.

As shown in FIG. 20, the actuator 1104 can comprise one or more apertures 1163. The actuator 1104 can comprise indicia 1165 to indicate whether the actuator 1104 and the sleeve 1106 are in an unlocked position or a locked position.

Figure 21:
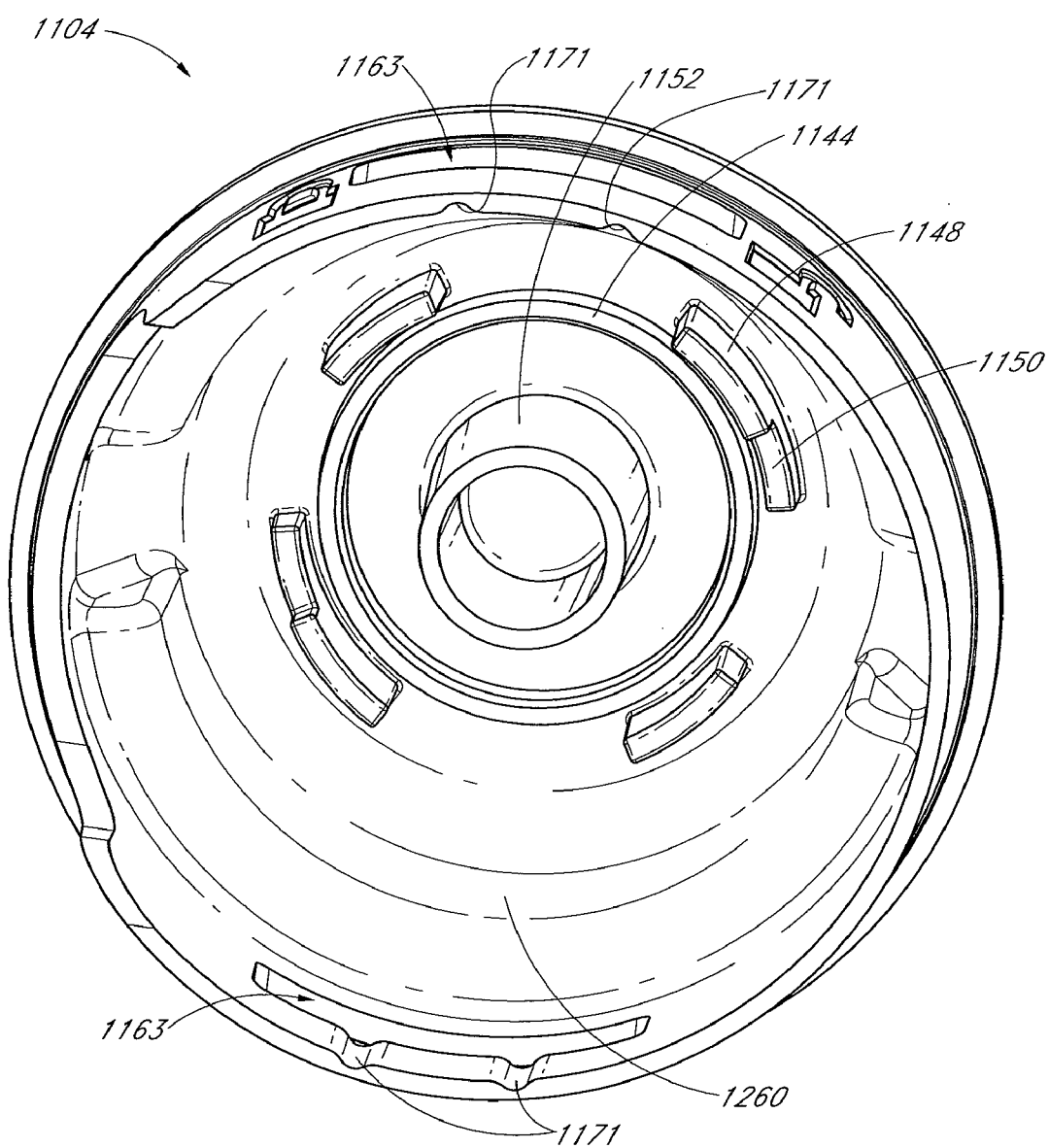
FIG. 21 is a lower perspective view of the actuator of FIG. 20.

With reference to FIG. 21, an interior of the actuator 1104 may comprise one or more displacement members 1144, one or more guideposts 1148, one or more travel-limiting members 1152, and one or more grooves or detents 1171. In some embodiments, the detents can have configurations other than that of grooves. In some embodiments, such as the embodiment illustrated in FIG. 21, the grooves 1171 can be positioned adjacent to the one or more apertures 1163.

Figure 22:
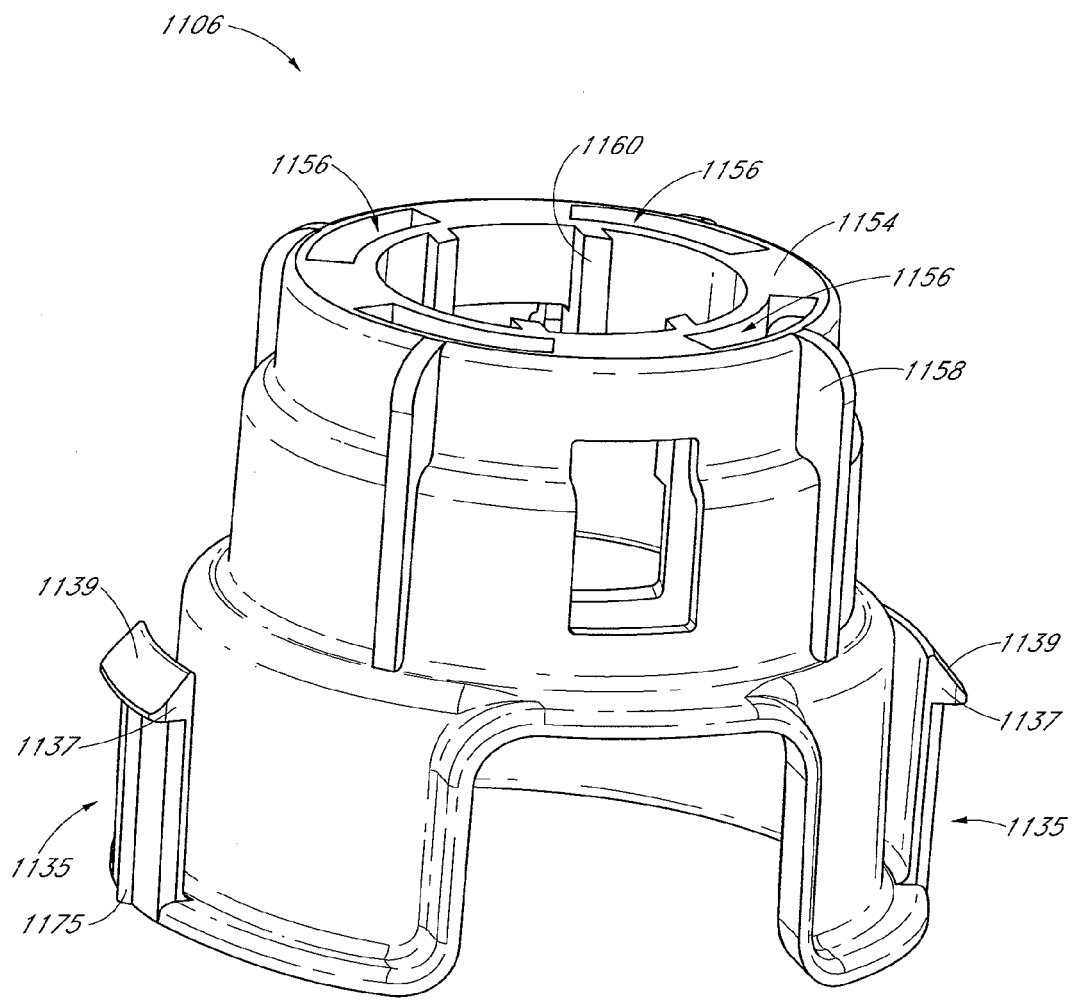
FIG. 22 is an upper perspective view of a sleeve of the insertion device of FIG. 18.
Figure 23:
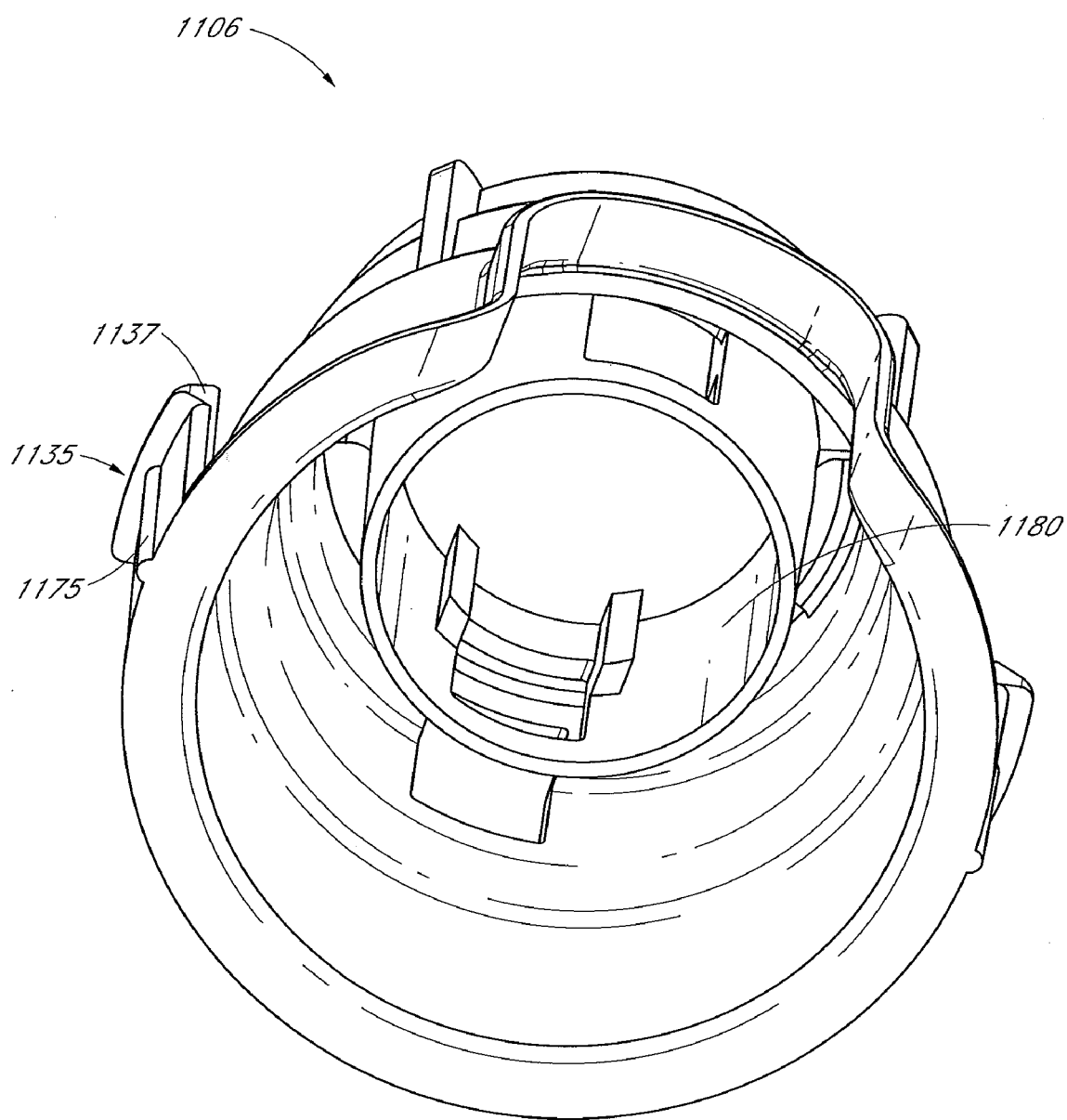
FIG. 23 is a lower perspective view of the sleeve of FIG. 22.

Referring to FIGS. 22 and 23, the sleeve 1106 can comprise one or more arms 1135. Each arm 1135 can comprise a foot 1137. The feet 1137 can be located at a terminal end of the arms 1135. Each foot can include a cam surface 1139. The feet 1137 can face outwardly, as illustrated in FIGS. 22 and 23, inwardly, circumferentially, or in other directions.

One or more of the arms 1135 can comprise a ridge 1175. The ridge 1175 can be located centrally on an arm 1135 and can extend partially or entirely from a base of the arm to a terminal end, as shown in FIGS. 22 and 23. In some embodiments, the ridge 1175 can be located close to an edge of the arm 1135. While the ridges 1135 illustrated in FIGS. 22 and 23 are primarily straight with constant heights and widths along their lengths, in other embodiments the ridges can be curved or have a non-constant widths or heights. In some embodiments, the ridges can be circular and can resemble a single generally circular bump or a series of bump, or have other configurations.

Referring again to FIG. 20, the one or more apertures 1163 of the actuator 1104 can be configured to permit a portion of one or more of the arms 1135, the feet 1137, the cam surfaces 1139, and the ridges 1175 of the sleeve 1106 (see FIGS. 22 and 23) to partially or fully extend through the apertures 1163. The one or more apertures 1163 can have a width that allows a foot 1137 of the sleeve 1106 to move within the aperture 1163 as the actuator 1104 is rotated with respect to sleeve 1106 between the locked position and the unlocked position.

The grooves 1171 can be configured to accept the ridge 1175 of the arm 1135 when the foot 1137 fully or partially extends through the aperture 1163. Rotation of the foot 1137 along with the arm 1135 relative to the aperture 1163 is accompanied by movement of the ridge 1175 relative to the grooves 1171. In this manner, the locked position can be indicated by engagement of the ridge 1175 with one of the grooves 1171, and the unlocked position can be indicated by engagement of the ridge 1175 with the other of grooves 1171. Additionally or alternatively, the locked position can be indicated by proximity of the foot 1137 to one of the indicia 1165 on the actuator 1104 as viewed through one of the apertures 1163.

In some embodiments, rotation of the arm 1135 relative to the aperture 1163 requires more force when the ridge 1175 is engaged with one of the grooves 1171. Thus, unintentional rotation of the actuator 1104 with respect to the sleeve 1106 can be inhibited, which unintentional rotation may accidentally unlock the device. Engagement of the ridge 1175 and one of the grooves 1171 can also provide tactile feedback to the user when the actuator 1104 is moved between the locked position and the unlocked position.

In other embodiments, the arm 1135 can comprise one or more grooves and the actuator 1104 can comprise one or more ridges with the one or more grooves and the one or more ridges being configured to cooperate. Other configurations can also be used. For example, the arm 1135 can comprise one or more detents and the actuator 1104 can comprise one or more bumps with the one or more detents and the one or more bumps being configured to cooperate.

Figure 24:
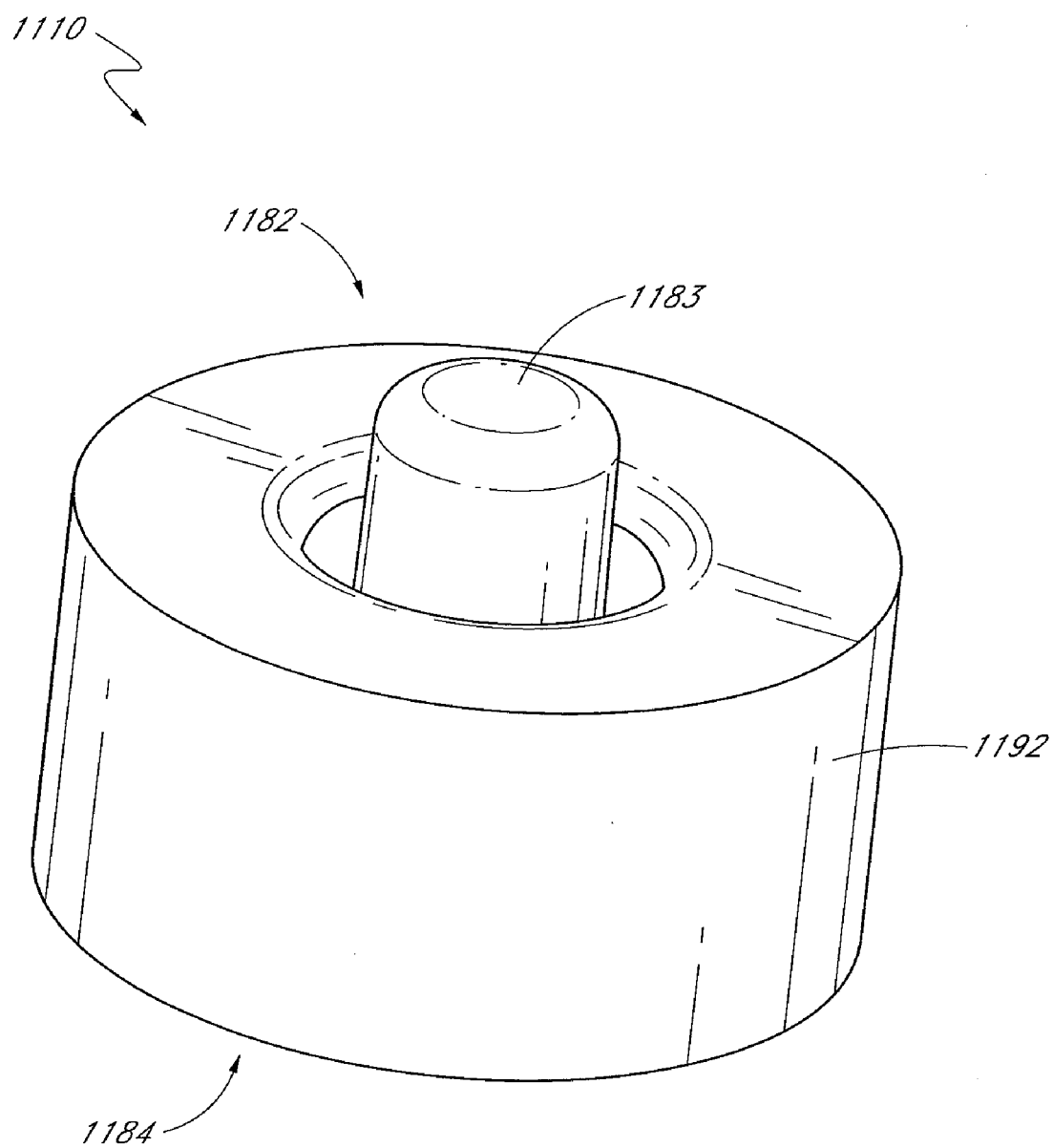
FIG. 24 is an upper perspective view of a needle hub of the insertion device of FIG. 18.
Figure 25:
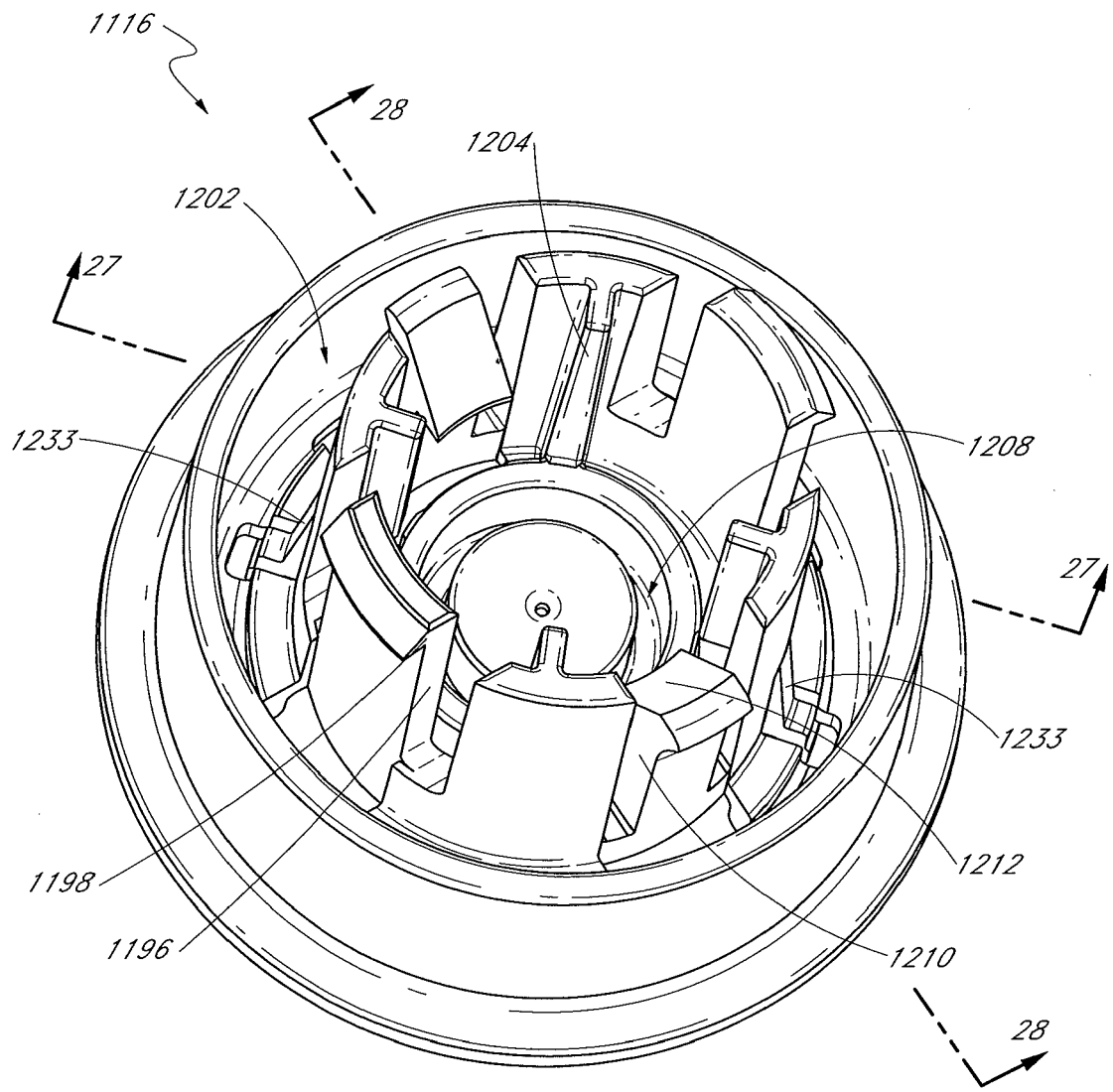
FIG. 25 is an upper perspective view of the shuttle of the insertion device of FIG. 18.
Figure 26:
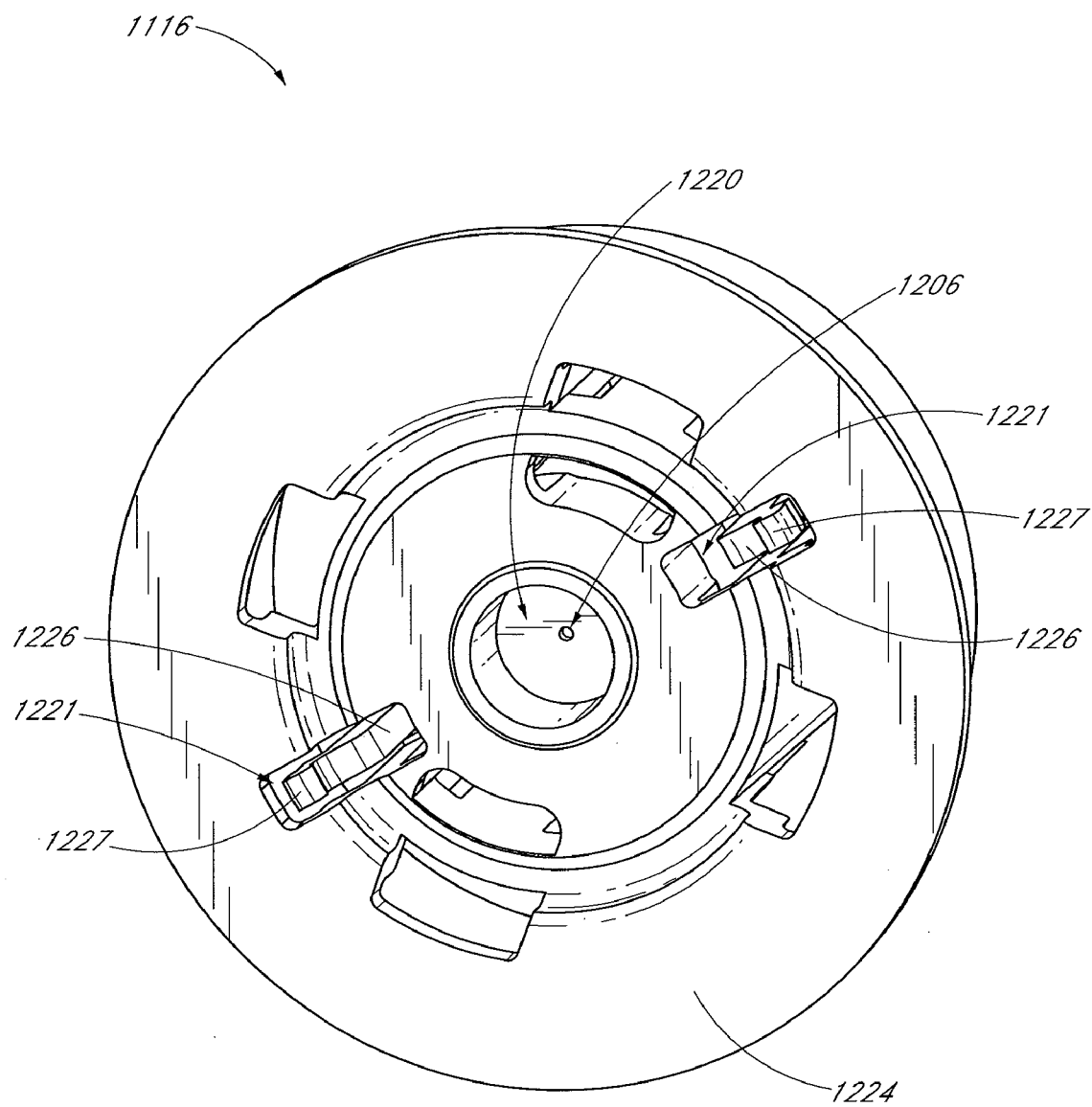
FIG. 26 is a lower perspective view of the shuttle of FIG. 25.
Figure 27:
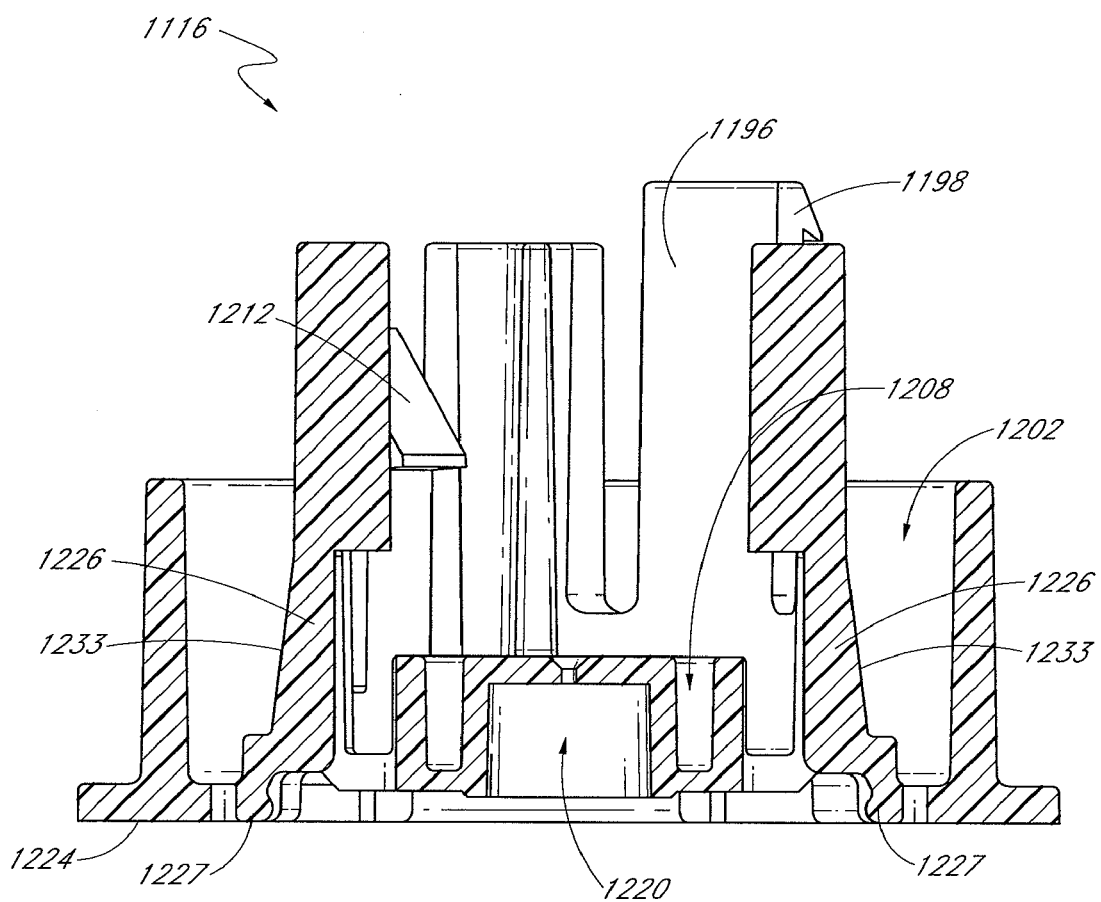
FIG. 27 is a cross-sectional view of the shuttle of FIGS. 25 and 26, taken along line 27-27 shown in FIG. 25.
Figure 28:
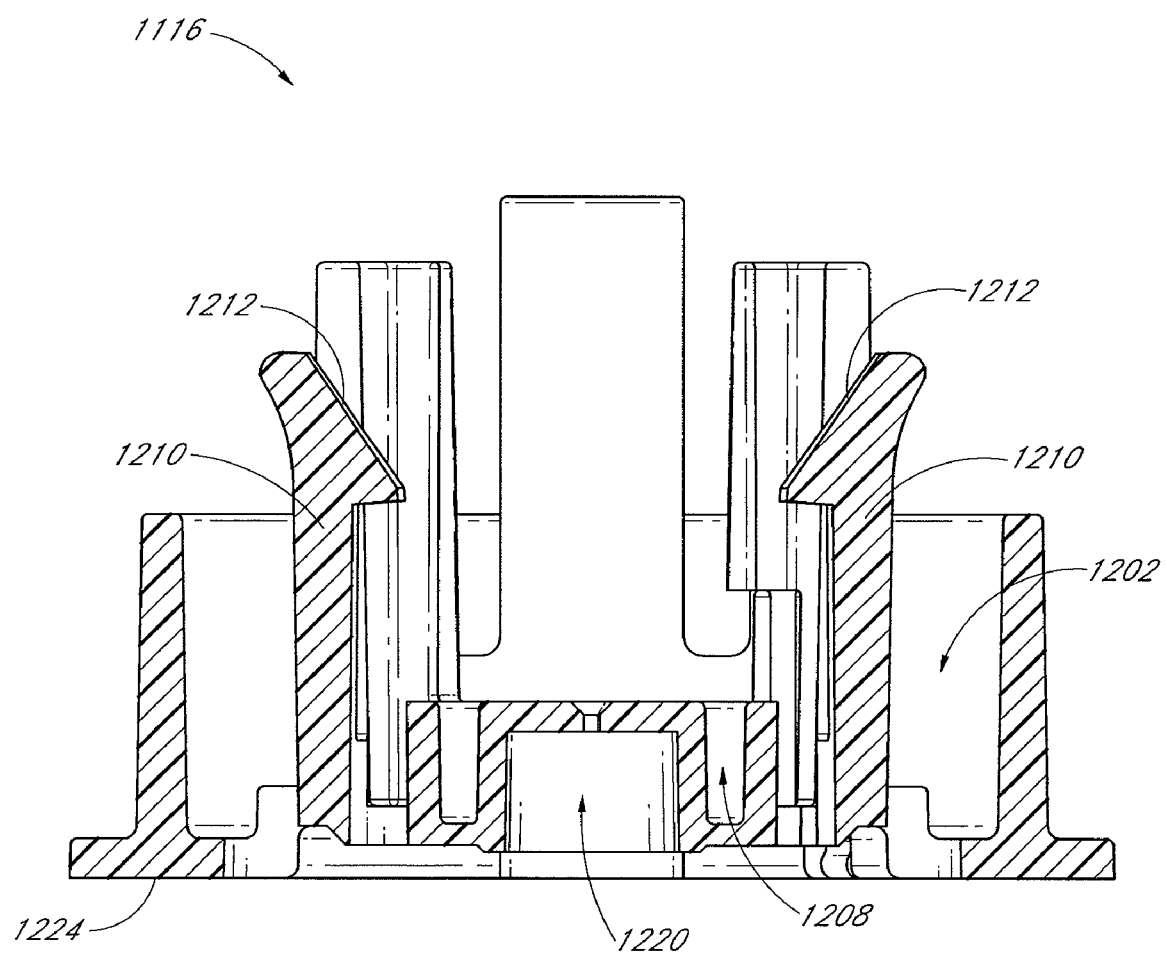
FIG. 28 is another cross-sectional view of the shuttle of FIGS. 25 and 26, taken along the line 28-28, shown in FIG. 25.
Figure 29:
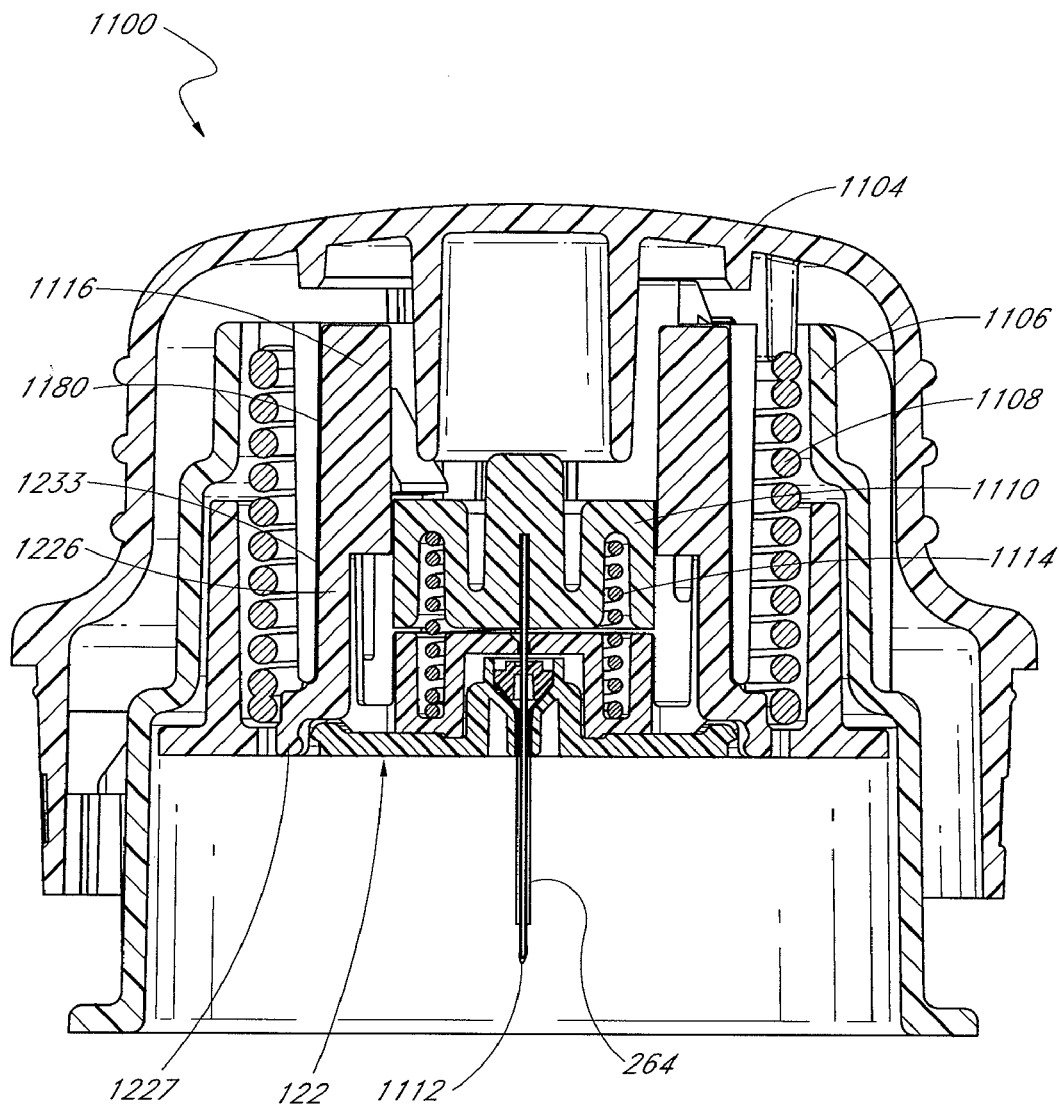
FIG. 29 is a cross-sectional view, similar to FIG. 27, of the insertion device of FIG. 18 before actuation.

FIG. 24 illustrates the needle hub 1110. In this embodiment, the needle hub 1110 comprises an upper side 1182, a lower side 1184, a cylindrical follower surface 1192, and a protrusion 1183. The protrusion 1183 can be positioned on the upper side 1182, as illustrated in FIG. 24, or can in other embodiments be located on the lower side 1184. The protrusion 1183 may aid in assembling the insertion device 1100. For example, it may facilitate proper orientation of the needle hub 1110 during assembly of the insertion device 1100. Additionally or alternatively, the protrusion 1183 may act as a handle for manipulating and stabilizing the needle hub during assembly.

FIGS. 25-28 illustrate the shuttle 1116. The shuttle 1116 can comprise one or more recesses 1202 that are configured to receive at least a portion of the insertion spring 1108. The shuttle 1116 can comprise one or more sleeve-engaging arms 1196 each having a sleeve-engaging foot 1198. The shuttle can comprise one or more cam surfaces 1204 configured to cooperate with the follower surface 1192 of the needle hub 1110 to orient the needle hub 1110 while permitting sliding movement of the needle hub 1110 relative to the shuttle 1116. The shuttle 1116 can comprise one or more recesses 1208 to receive at least a portion of the retraction spring 1114. The shuttle can comprise one or more needle-hub-engaging arms 1210, each having a needle-hub-engaging foot 1212.

The shuttle 116 can comprise a recess 1220 to receive at least a portion of an infusion device 102, such as an infusion set. The recess 1220 can be positioned such that the needle 1112 extends through the needle aperture 1206 and through the cannula 264 of the base 122. The shuttle 1116 can also comprise additional surfaces such as surfaces 1222 and 1224, to engage the infusion device 102.

In some embodiments, the shuttle 1116 can comprise one or more base-retaining arms 1226, such as those illustrated in FIGS. 25-28, to engage the infusion device 102. In some embodiments, the base-retaining arms 1226 can be positioned in base-retaining arm recesses 1221. The arms 1226 can include base-retaining feet 1227, to clamp, grasp, or otherwise engage the base 122 and secure it to the shuttle 1116. The base-retaining feet 1227 can be substantially flat or in other embodiments can be concave or have other shapes. The base-retaining arms 1226 can include sleeve-engagement surfaces 1233 positioned for engagement by the cam surface 1180 of the sleeve 1106 to urge the base-retaining feet 1227 toward the base 122 to impede unintentional disengagement of the infusion device 102 from the shuttle 1116. In some embodiments, the base-retaining feet 1227 can be configured such that when the cam surface 1180 is engaged with the sleeve-engagement surfaces 1233, the base-retaining feet 1227 extend beneath a bottom edge of the base 122, thereby physically inhibiting separation of the infusion device 102 from the shuttle 1116.

The insertion device 1100 can be used as follows. After preparing an injection site on the skin, the user can remove a protective paper backing, if any, from an adhesive of the base 122. The sleeve 1106 can then be rotated relative to the actuator 1104 from the locked position to the unlocked position and a lower surface 1176 of the sleeve 1106 can be placed on the skin at the injection site.

Figure 30:
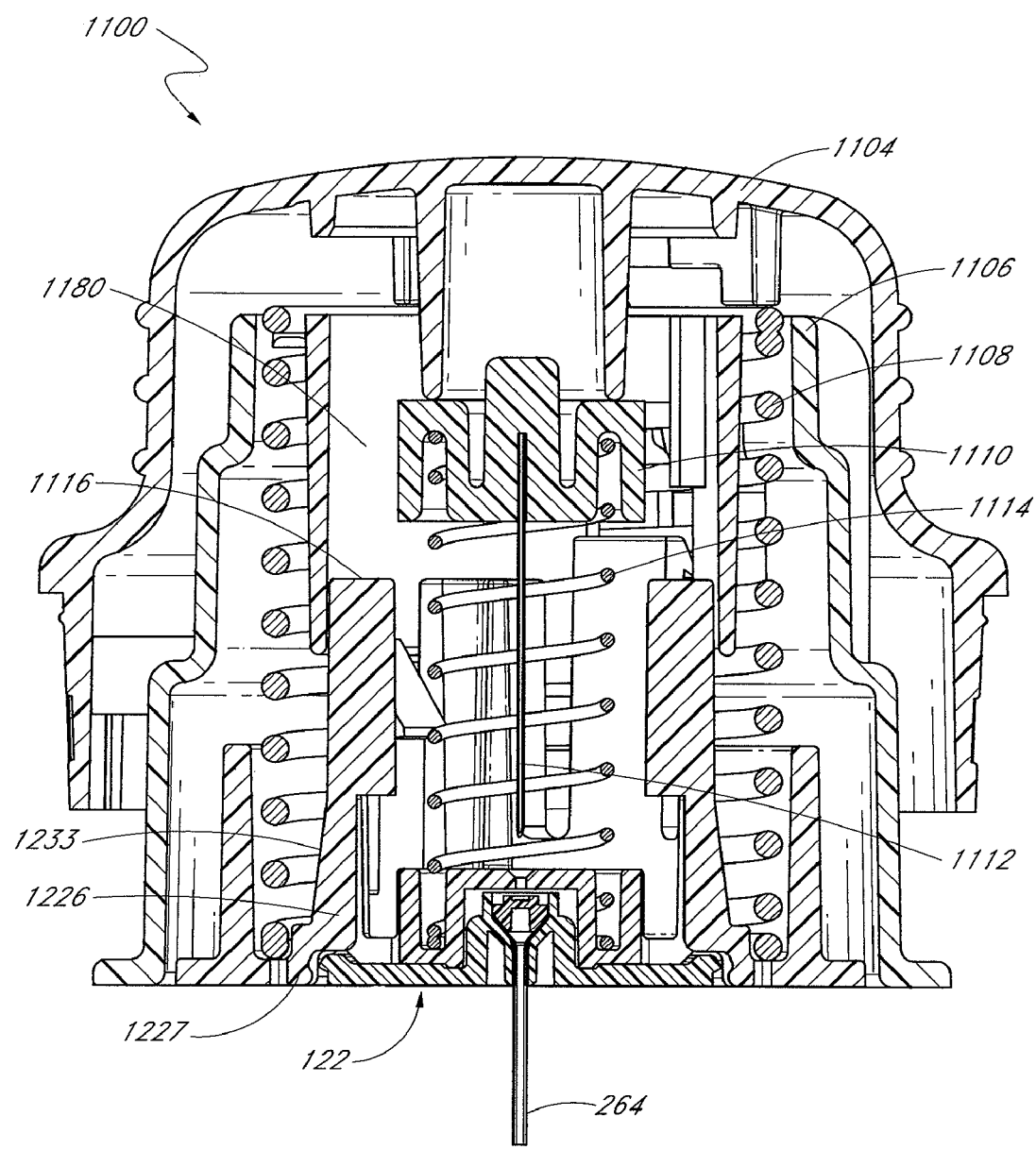
FIG. 30 is a cross-sectional view, similar to FIGS. 27 and 29, of the insertion device of FIG. 18 after actuation.

The actuator 1104 can be advanced toward the skin, with the external guide rails 1158 of the sleeve 1106 guiding the actuator 1104 as it is advanced. The actuator 1104 can compress the insertion spring 1108 until an engagement surface 1146 of the displacement member 1144 of the actuator 1104 presses against cam surfaces 1200 of the sleeve-engaging feet 1198 of the shuttle 1116 to force the sleeve-engaging feet 1198 off of an upper surface 1154 of the sleeve 1106 to allow the shuttle 1116 to advance within the sleeve 1106. The orientation of the shuttle 1116 within the sleeve 1106 can be preserved as the shuttle 1116 advances by cooperation of internal guide rails 1160 in cooperation with slots 1218 of the shuttle 1116. Advancement of the shuttle 1116 within sleeve 1106 can be limited by the engagement of the sleeve-engaging feet 1198 against one or more stop ledges 1262 of the sleeve 1106 (see FIG. 30).

As the shuttle 1116 advances through the sleeve 1106, the sleeve-engagement surfaces 1233 of the shuttle 1116 can advance downwardly relative to the cam surface 1180 of the sleeve 1106. The base-retaining arms 1226 can spread outwardly when the sleeve-engagement surfaces 1233 of the shuttle 1116 clear the cam surface 1180 of the sleeve 1106. The base-retaining feet 1227 can move away from the base 122 as the base-retaining arms 1126 spread outwardly such that the base 122 can be released from the shuttle 1116.

As the shuttle 1116 approaches or arrives at the end of its range of travel within the sleeve 1106, the needle-hub-engaging arms 1210 can clear the cam surface 1180 of the sleeve 1106 to allow the needle-hub-engaging arms 1210 to move away from the needle hub 1110. Once the needle hub 1110 is released by the needle-hub-engaging arms 1210, the retraction spring 1114 can push the needle hub 1110 away from the shuttle 1116 to draw the needle 1112 within the insertion device 1100. The guide surfaces 1204 of the shuttle 1116 can orient the needle hub 1110 as it moves away from the shuttle 1116 so that the needle 1112 can be withdrawn substantially linearly (e.g., straightly) from the patient's skin. Thus, the needle 1112 can be protected both before and after insertion of the base 122 to prevent accidental needle sticks. This automatic retraction feature can ensure that the needle 1212 is only exposed while the infusion device 102 is being inserted.

Surfaces 1222 or 1224 of the shuttle 1116, or both, can press the base 122 against the skin. The user may maintain pressure against the cap 104 so that the surfaces 1222 and 1224 of the shuttle 1116 can hold the base 122 against the skin to ensure good adhesion between the base 122 and the skin. Thereafter, the user may lift the insertion device 1100 away from the skin leaving the base 122 against the skin with the cannula extending through the skin.

Once the insertion device 1100 is removed from the skin, the protective cap 1118 can be engaged with the actuator 1104 for safe disposal of the needle 1112 within the insertion device 1100.

In some embodiments, the insertion device 1100 can be used to insert an infusion device 102, such as an infusion set, having a rigid infusion cannula 264, such as those described in United States Patent Application Publication No. 2007/0185441, which is hereby incorporated by reference herein in its entirety. Such embodiments of the insertion device 1100 may omit the needle 1112 if the infusion cannula 264 has sufficient rigidity to pierce the skin. Additionally, in embodiments of the insertion device 1100 wherein movement of the needle hub 1110 within the insertion device 1100 does not affect securement of the base 122 of the infusion device 102 to the shuttle 1116, the needle hub 1110 and the retraction spring 1114 may be omitted. If these components are omitted, corresponding simplifications to the structure of the shuttle 1116 may also be made. Other components, structures, or processes can be omitted in these and other embodiments.

The examples shown in the drawings of this application and described in the text are not intended to be limiting, but merely to illustrate various aspects of certain embodiments. Many other alternatives and configurations are possible, and are encompassed by this disclosure. Moreover, each of the components and features described herein with respect to each embodiment can be used in other embodiments of this disclosure to form additional embodiments not expressly illustrated or described. In addition, no component, structure, or process disclosed herein is indispensible or critical.

What is claimed is:

1. A device for inserting an infusion device through skin for subcutaneous infusion, comprising:
    a sleeve having an upper surface and a lower surface, the lower surface being configured to engage skin;
    a shuttle having an upper side and a lower side, the shuttle comprising a receptacle on its lower side for accommodating an infusion device, at least a first movement-restraining arm, and a least a first hub-retaining arm, and an internal cavity configured to receive a hub, the internal cavity comprising a horizontal cross-sectional area, the shuttle being movable between a retracted position and an advanced position, the first movement-restraining arm engaging the upper surface of the sleeve when the shuttle is in the retracted position to inhibit movement of the shuttle toward the advanced position;
    at least a first biasing member operatively connected to the shuttle to urge the shuttle toward the advanced position;
    the hub positioned above the upper side of the shuttle, the hub having an upper side and a lower side, and a horizontal cross-sectional area that is constant in a first position and a second position, the horizontal cross-sectional area of the hub being smaller than the horizontal cross-sectional area of the internal cavity of the shuttle, the hub being movable between the first position and the second position with respect to the shuttle, the first hub-retaining arm of the shuttle inhibiting movement of the hub away from the shuttle when the hub is in the first position and the shuttle is in the retracted position;
    a needle having an upper end and a lower end, the upper end being fixedly attached to the lower side of the hub, the lower end being configured to pierce skin, the lower end of the needle extending below the lower surface of the sleeve when the shuttle is in the advanced position and the hub is in the first position, the lower end of the needle being positioned above the lower surface of the sleeve when the hub is in the second position;
    at least a second biasing member operatively connected to the hub to urge the hub upwardly from the shuttle away from the lower surface of the sleeve;
    an actuator being movably attached to the sleeve such that, when the first movement-restraining arm is engaged with the upper surface, advancement of the actuator toward the sleeve permits disengagement of the first movement-restraining arm of the shuttle from the upper surface of the sleeve;
    wherein disengagement of the first movement-restraining arm of the shuttle from the upper surface of the sleeve allows the first biasing member to move the shuttle from the retracted position to the advanced position; and
    wherein movement of the shuttle from the retracted position to the advanced position allows the first hub-retaining arm of the shuttle to release the hub such that the second biasing member moves the hub from the first position to the second position;
    wherein the device is configured to be used only once.

2. The device of claim 1, wherein the sleeve further comprises at least one aperture and the actuator further comprises at least one protrusion, wherein the at least one aperture and the at least one protrusion are configured such that the actuator and the sleeve can be rotated between a first position in which the actuator is inhibited from moving toward the lower surface of the sleeve and a second position in which the actuator is movable toward the lower surface to disengage the first movement-restraining arm of the shuttle from the upper surface of the sleeve.

3. The device of claim 2, wherein the at least one aperture is located in the upper surface of the sleeve and the at least one protrusion extends downwardly from a lower side of the actuator.

4. The device of claim 1, wherein the shuttle further comprises at least one movable member for engaging the infusion device to inhibit release of the infusion device from the shuttle before the first movement-restraining arm of the shuttle is disengaged from the upper surface of the sleeve.

5. The device of claim 4, wherein the at least one movable member is configured to be engaged by the hub when the hub is in the first position such that the movable member is urged against the infusion device to inhibit release of the infusion device from the shuttle before the first movement-restraining arm of the shuttle is disengaged from the upper surface of the sleeve.

6. The device of claim 4, wherein the at least one movable member is configured to be engaged by a cam surface of the sleeve when the shuttle is in the retracted position to cause contact between the movable member and the infusion device to inhibit release of the infusion device from the shuttle before the first movement-restraining arm of the shuttle is disengaged from the upper surface of the sleeve.

7. The device of claim 1, wherein the shuttle is received at least partially within the sleeve.

8. The device of claim 1, wherein the first biasing member comprises a spring positioned between the sleeve and the shuttle.

9. The device of claim 1, wherein the hub is received at least partially within the shuttle.

10. The device of claim 1, wherein the second biasing member comprises a spring positioned between the shuttle and the hub.

11. An inserter for placing an infusion device at least partially into skin, comprising:
- a sleeve having a bottom surface, the bottom surface being configured to engage skin;
- a carriage having an upper side and a lower side, the carriage being configured for carrying an infusion device on its lower side, the carriage positioned at least partially within the sleeve, the carriage being movable between a retracted position and an advanced position, a lowest portion of the infusion device being spaced upwardly from the bottom surface of the sleeve when the carriage is in the retracted position, a bottom portion of the infusion device extending below the lower surface of the sleeve when the carriage is in the advanced position;
- at least a first biasing member operatively connected to the carriage to urge the carriage toward the advanced position;
- a hub and a needle, the hub being positioned above the upper side of the carriage, the hub being movable between a first position and a second position with respect to the carriage, the needle having an upper end and a lower end, the upper end being fixedly attached to the lower side of the hub, the lower end being configured to pierce skin, the needle extending below the carriage when the hub is in the first position, the lower end of the needle extending no lower than the carriage when the hub is in the second position;
- at least a second biasing member operatively connected to the hub to urge the hub upwardly from the carriage away from, the lower surface of the sleeve;
- an actuator operatively connected to the sleeve to cause the first biasing member to move the carriage from the retracted position to the advanced position;
- wherein movement of the carriage from the retracted position toward the advanced position permits the hub to move from the first position to the second position, the carriage having a cavity configured to receive the hub, wherein the cavity has a horizontal cross-sectional area larger than a horizontal cross-sectional area of the hub, the horizontal cross-sectional area of the hub being constant in the first and second positions;
- wherein the carriage further comprises at least a first arm configured to engage the hub to inhibit movement of the hub from the first position to the second position, the first arm being held in engagement with the hub at least until the lower end of the needle advances below the bottom surface of the sleeve;
- wherein the device is configured to be used only once.

12. The inserter of claim 11, wherein the inserter is configured to be removed from the infusion device before infusion commences.

13. The inserter of claim 11, wherein the carriage further comprises at least a second arm configured to engage the sleeve to inhibit movement of the carriage from the retracted position to the advanced position, the second arm being engageable by the actuator such that the actuator can disengage the second arm from the sleeve to permit the first biasing member to urge the carriage from the retracted position to the advanced position.

14. The inserter of claim 11, wherein the first biasing member engages the carriage and the actuator.

15. The inserter of claim 11, wherein the second biasing member engages the carriage and the hub.

16. The inserter of claim 11, wherein a surface of the insertion device is pressed against an exterior surface of the skin when the carriage is in the advanced position.

17. The inserter of claim 16, wherein the surface of the insertion device is an adhesive surface.

18. An inserter for placing an infusion device at least partially into skin, comprising:
- a housing having a bottom surface, the bottom surface being configured to engage skin;
- a carriage having a first side and a second side, the carriage being configured to carry an infusion device on the first side, the carriage positioned at least partially within the housing, the carriage being movable between a retracted position and an advanced position, a lowest portion of the infusion device being spaced upwardly from the bottom surface of the housing when the carriage is in the retracted position, a bottom portion of the infusion device extending below the lower surface of the housing when the carriage is in the advanced position, the carriage comprising at least one movable member for engaging the infusion device to inhibit release of the infusion device from the carriage before the carriage moves from the retracted position toward the advanced position;
- at least a first biasing member operatively connected to the carriage to urge the carriage toward the advanced position;
- a hub and a needle that is attached to the hub, the hub being positioned on the second side of the carriage;
- an actuator operatively connected to the housing to cause the first biasing member to move the carriage from the retracted position to the advanced position;
- wherein the carriage further comprises at least a first arm configured to engage the hub such that movement of the hub from a first position to a second position is inhibited at least until the lower end of the needle advances below the bottom surface of the sleeve, the carriage further comprising a cavity configured to receive the hub, the cavity having a horizontal cross-sectional area larger than a horizontal cross-sectional area of the hub, the horizontal cross-sectional area of the hub being constant in the first and second positions.

19. The device of claim 18, wherein the at least one movable member is configured to be engaged by a cam surface of the housing when the carriage is in the retracted position to cause contact between the movable member and the infusion device to inhibit release of the infusion device from the carriage before the carriage moves from the retracted position toward the advanced position.

20. The device of claim 19, wherein the at least one movable member engages the infusion device near an outer periphery of the infusion device.

21. The device of claim 18, wherein the at least one movable member is configured to be engaged by the hub when the hub is in the first position such that the movable member is urged against the infusion device to inhibit release of the infusion device from the carriage before the carriage moves from the retracted position toward the advanced position.

22. The device of claim 18, wherein the at least one movable member further comprises at least one foot configured to extend under at least a portion of the infusion device when the carriage is in the retracted position.

* * * * *